United States Patent
Helland et al.

(10) Patent No.: US 8,992,954 B2
(45) Date of Patent: Mar. 31, 2015

(54) COMPOSITIONS COMPRISING A DERIVATIVE OF 5-AMINOLEVULINIC ACID

(75) Inventors: Oddveig Sellæg Helland, Oslo (NO); Stig Ove Johnsen, Oslo (NO); Enrique Alabata, Torrance, CA (US); Anja J. Jentoft, Oslo (NO); Aslak Godal, Oslo (NO)

(73) Assignee: Photocure ASA, Oslo (NO)

( * ) Notice: Subject to any disclaimer, the term of this patent is extended or adjusted under 35 U.S.C. 154(b) by 213 days.

(21) Appl. No.: 13/038,305

(22) Filed: Mar. 1, 2011

(65) Prior Publication Data

US 2011/0212146 A1 Sep. 1, 2011

Related U.S. Application Data

(60) Provisional application No. 61/309,313, filed on Mar. 1, 2010.

(30) Foreign Application Priority Data

Mar. 1, 2010 (EP) .................................... 10250363

(51) Int. Cl.
| | | |
|---|---|---|
| A61K 8/02 | (2006.01) | |
| A61K 9/00 | (2006.01) | |
| A61K 31/19 | (2006.01) | |
| A61K 8/44 | (2006.01) | |
| A61K 8/06 | (2006.01) | |
| A61K 8/92 | (2006.01) | |
| A61Q 17/04 | (2006.01) | |
| A61Q 19/08 | (2006.01) | |

(52) U.S. Cl.
CPC ... *A61K 8/44* (2013.01); *A61K 8/06* (2013.01); *A61K 8/92* (2013.01); *A61Q 17/04* (2013.01); *A61Q 19/08* (2013.01); *A61K 2800/522* (2013.01); *A61K 2800/88* (2013.01)
USPC ............................ 424/401; 424/400; 514/574

(58) Field of Classification Search
CPC ................... A61K 2800/522; A61K 2800/88; A61K 8/06; A61K 8/44; A61K 8/92; A61Q 17/04; A61Q 19/08
USPC .................................... 424/400, 401; 514/574
See application file for complete search history.

(56) References Cited

U.S. PATENT DOCUMENTS

| | | | |
|---|---|---|---|
| 5,207,998 A * | 5/1993 | Robinson et al. ............... | 424/59 |
| 5,520,905 A | 5/1996 | Uhlmann et al. | |
| 6,034,267 A * | 3/2000 | Gierskcky et al. ............ | 560/155 |
| 6,750,212 B2 | 6/2004 | Peng et al. | |
| 7,217,736 B2 | 5/2007 | Klaveness et al. | |
| 7,348,361 B2 | 3/2008 | Marti et al. | |
| 7,563,819 B1 | 7/2009 | Klaveness et al. | |
| 2007/0225518 A1* | 9/2007 | Malik et al. ........................ | 562/8 |
| 2008/0146667 A1 | 6/2008 | Kreindel | |
| 2012/0134921 A1* | 5/2012 | Helland et al. ............... | 424/1.61 |
| 2012/0136055 A1* | 5/2012 | Stensrud ....................... | 514/551 |

FOREIGN PATENT DOCUMENTS

| | | |
|---|---|---|
| WO | WO 96/28412 | 9/1996 |
| WO | 99/22802 | 5/1999 |
| WO | WO 99/53962 | 10/1999 |
| WO | 01/85125 | 11/2001 |
| WO | WO 02/09690 | 2/2002 |
| WO | WO 02/10120 | 2/2002 |
| WO | WO 02/078687 | 10/2002 |
| WO | WO 03/011265 | 2/2003 |
| WO | WO 03/041673 | 5/2003 |
| WO | 2005/092838 | 10/2005 |
| WO | WO 2005/092838 | 10/2005 |
| WO | WO 2006/051269 | 5/2006 |
| WO | 2008/084241 | 7/2008 |
| WO | WO 2008/084241 | 7/2008 |
| WO | 2008/106966 | 9/2008 |
| WO | WO 2008/106983 | 9/2008 |
| WO | WO 2009/074811 | 6/2009 |
| WO | WO 2009/077960 | 6/2009 |
| WO | WO 2010/072419 | 7/2010 |
| WO | WO 2010/078929 | 7/2010 |
| WO | WO 2010/142456 | 12/2010 |
| WO | WO 2010/142457 | 12/2010 |

OTHER PUBLICATIONS

C. Zane et al., "Clinical and Echographic Analysis of Photodynamic Therapy Using Methylaminolevulinate as Sensitizer in the Treatment of Photodamaged Facial Skin," Lasers in Surgery and Medicine 39:203-209 (2007), pp. 204-209.

* cited by examiner

*Primary Examiner* — Aradhana Sasan
(74) *Attorney, Agent, or Firm* — Kenyon & Kenyon LLP

(57) ABSTRACT

The present invention relates to compositions comprising a derivative of 5-aminolevulinic acid (5-ALA), e.g. an ester of 5-ALA or a skin compatible salt thereof. Further, the invention relates to use of such compositions in methods of cosmetic treatment, particularly in methods of improving or otherwise enhancing the appearance of the skin.

30 Claims, No Drawings

COMPOSITIONS COMPRISING A DERIVATIVE OF 5-AMINOLEVULINIC ACID

CROSS-REFERENCE TO RELATED APPLICATIONS

The present application claims the benefit of U.S. Provisional Application No. 61/309,313, filed on Mar. 1, 2010, which is expressly incorporated herein in its entirety by reference thereto.

The present invention relates to compositions comprising a derivative of 5-aminolevulinic acid (5-ALA), e.g. an ester of 5-ALA or a skin compatible salt thereof. Further, the invention relates to use of such compositions in methods of cosmetic treatment, particularly in methods of improving or otherwise enhancing the appearance of the skin.

In today's society there is an ever increasing desire for both men and women, especially women, to appear youthful. The condition and overall appearance of the skin is an indication of youthfulness; the effects of skin aging, such as wrinkles or fine lines, are of great concern for many people.

Aging of the skin is the result of more than just chronological age; it is also a result of external factors, for example, environmental conditions such as exposure to the sun's ultraviolet rays. Aging results in skin changes including roughness, sallowness, mottled pigmentation, diffuse facial redness, telangiectasias and the formation of fine lines or wrinkles, collectively referred to as "photoaging". As a reminder of the loss of youth, such skin changes are generally considered non-aesthetic.

A frequent exposure to ultraviolet radiation may result in photodamages which are considered disease states such as actinic keratosis (AK), a pre-malignant condition of thick, scaly, or crusty patches of skin. Since some of these precancers progress to squamous cell carcinoma, they are usually treated. One of the treatments for AK is topical photodynamic therapy with 5-aminolevulinic acid (5-ALA) (Levulan® Kerastick®, Dusa Pharmaceuticals) or a derivative of 5-ALA, 5-ALA methyl ester (Metvix®, Galderma). While such treatment has proven to be very effective, it has also been observed that it offered an excellent cosmesis, i.e. resulted in an overall photochemorejuvenation of the skin with improvement of mottled pigmentation, sallowness and fine lines (see C. Zane et al., Lasers in Surgery and Medicine 39:203-209 (2007).

There have been several suggestions of cosmetic treatments with compositions comprising 5-ALA or derivatives thereof:

U.S. Pat. No. 5,520,905 discloses a method to protect the skin from the damages of the sun and to alleviate such damages by using a cosmetic or dermal preparation comprising 0.01 to 10% of 5-ALA. Such a composition was found to act as an antioxidant and radical inhibitor since it can provide protection against uncontrolled oxidation processes which are photochemically induced and even quench singlet oxygen.

WO 2008/106983 discloses a method for non-therapeutic (i.e. cosmetic) and therapeutic treatment of the skin wherein a liposomal liquid preparation of a photosensitizes like 5-ALA or a 5-ALA derivative in a concentration of 0.1 to 2% is used. In order to get the desired cosmetic result, the preparation is delivered to the target area in the form of a number of repeated spray doses over a time period of 1 to 3 hours (Examples 2 and 3). Longer time periods i.e. 3 hours vs. 1 hour and more frequent spray doses, i.e. every $5^{th}$ minute over 2 hours vs. every $15^{th}$ minute over 2 hours were found to be more efficient in terms of rejuvenation.

WO 02/078687 discloses cosmetic photodynamic methods, i.e. methods for stimulating the tanning of the skin. Topical preparations for use in these methods contain 5-ALA in a range of 0.1 to 30% by weight based on the total weight of the preparation. Experimental data were obtained by volunteers using Eucerin™ cream base containing 5%, 10% and 20% by weight of ALA. The cream was applied under occlusion to the skin. After 4 hours, the skin was irradiated with visible light. All volunteers complained about burning and itching during illumination, erythema and edema appeared after the illumination. Also, pigmentary response was observed.

US 2008/146667 discloses methods of cosmetic treatment such as skin rejuvenation wherein compositions comprising photolabile compounds such as 5-ALA and derivatives thereof in a concentration of lower than 20% w/w, preferably lower than 2% w/w are used. The photolabile compounds are activated by exposure to sunlight. We have now surprisingly found that compositions containing 5-ALA derivatives, preferably 5-ALA esters or skin compatible salts thereof, are effective in enhancing and improving the appearance of the skin of a mammalian subject, preferably a human subject. In particular, we have found that such compositions are effective in reducing the appearance of crow's feet, dark circles, fine lines, wrinkles, decreasing pore size and improving skin firmness and elasticity. The aforementioned results were achieved with minimum of undesirable side-effects like e.g. pain, itching, burning, erythema and/or edema both during and subsequent to application. Such side effects have been observed during and subsequent to skin treatments with compositions comprising 5-ALA or derivatives of 5-ALA, such as Levulan® Kerastick® or Metvix® (see for instance package inserts).

Thus, viewed from a first aspect the invention provides a composition comprising
   a) 2% by weight or less of a derivative of 5-ALA or skin compatible salts thereof
   b) 70% by weight or more of water;
   c) 2-25% by weight of at least one lipid carrier; and
   d) one or more emulsifiers.

The composition above is a dermal composition, i.e. a composition, e.g. a cosmetic or pharmaceutical composition, for use on the skin of a mammal, preferably a human. As such, the compositions according to the invention are compatible with the skin of a human, but also compatible with mucous membranes, the nails and/or the hair. The composition of the invention preferably exhibits a pleasant color, odor and texture. The term "texture" is understood as meaning those properties of the composition which are perceived by the sense of touch and relate to the structure and consistency of said composition.

The term "5-ALA" denotes 5-aminolevulinic acid, i.e. 5-amino-4-oxo-pentanoic acid.

The term "treatment" as used herein in relation to any use of a composition, product or kit or in relation to any method denotes a cosmetic or therapeutic treatment, preferably a cosmetic treatment.

The term "cosmetic" as used herein in relation to any composition, product, kit, method or use is intended to define a product or treatment method which is used or intended for use for cosmetic purposes, i.e. to enhance, improve or maintain the general cutaneous appearance of the individual to whom it is administered.

The term "5-ALA derivative" denotes chemically modified 5-ALA, i.e. 5-ALA having undergone a chemical derivation such as substitution of a chemical group or addition of a further chemical group to change any of its physico-chemical properties, such as solubility or bioavailability. Chemical derivation is preferably carried out at the carboxy group of 5-ALA, at the amino group of 5-ALA or at the keto group of 5-ALA, more preferably at the carboxy group or the amino group of S-ALA. Preferred derivatives include esters, amides and ether derivatives of 5-ALA, most preferred esters of 5-ALA.

The term "skin compatible salt" denotes a salt that is suitable for being used in a dermal composition, e.g. cosmetic or pharmaceutical composition for use on the skin of mammals, especially humans. A skin compatible salt is usually non-irritant and well-tolerated. Preferably, skin compatible salts are physiologically acceptable salts, i.e. salts which are physiologically tolerated if used in mammals and/or humans.

The term "% by weight" denotes the proportion of compounds in a composition in percent based on the total weight of the composition. The overall total is adding up to 100%.

The use of derivatives of 5-ALA, e.g. 5-ALA esters and salts thereof, in pharmaceutical products for use in photodynamic therapy or photodynamic diagnosis is well known in the scientific and patent literature, see, for example, WO 2006/051269, WO 2005/092838, WO 03/011265, WO 02/09690, WO 02/10120 and U.S. Pat. No. 6,034,267, the contents of which are incorporated herein by reference.

5-ALA derivatives useful in accordance with the invention may be any derivative of 5-ALA capable of providing the desired effect herein described. Such 5-ALA derivatives are preferably 5-ALA esters.

5-ALA esters, amino-substituted 5-ALA esters and skin compatible salts thereof, are among the preferred compounds for use in the invention described herein. Those compounds in which the 5-amino group is unsubstituted, i.e. 5-ALA esters, are particularly preferred. Such compounds are generally known and described in the literature, for example, WO 96/28412, WO 02/10120, WO 2003/041673 and WO 2009/077960, the contents of which are incorporated herein by reference, all describe 5-ALA derivatives which may be used in cosmetic compositions according to the invention.

Esters of 5-ALA resulting from the reaction of 5-ALA with substituted or unsubstituted alkanols, i.e. 5-ALA alkyl esters and substituted alkyl esters, and skin compatible salts thereof, are especially preferred derivatives of 5-ALA for use in the composition of the invention. Examples of such compounds include those of formula I and skin compatible salts thereof:

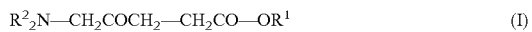

$$R^2{}_2N-CH_2COCH_2-CH_2CO-OR^1 \quad (I)$$

wherein
$R^1$ represents a substituted or unsubstituted alkyl group; and $R^2$ each independently represents a hydrogen atom or a group $R^1$ As used herein, the term "alkyl", unless stated otherwise, includes any long or short chain, cyclic, straight-chained or branched saturated aliphatic hydrocarbon group.

Unless stated otherwise, such alkyl groups may contain up to 40 carbon atoms. However, alkyl groups containing up to 30 carbon atoms, preferably up to 10, particularly preferably up to 8 and even more particularly up to 6, are preferred.

In compounds of formula I, the $R^1$ groups are substituted or unsubstituted alkyl groups. If $R^1$ is a substituted alkyl group, one or more substituents are either attached to the alkyl group and/or interrupt the alkyl group. Suitable substituents that are attached to the alkyl group are those selected from hydroxy, alkoxy, acyloxy, alkoxycarbonyloxy, amino, aryl, nitro, oxo, fluoro, chloro, —$SR^3$, —$NR^3{}_2$ and —$PR^3{}_2$, wherein $R^3$ is a hydrogen atom or a $C_{1-6}$ alkyl group. Suitable substituents that interrupt the alkyl group are those selected from —O—, —$NR^3$—, —S— or —$PR^3$—.

In a preferred embodiment, $R^1$ is an alkyl group substituted with one or more aryl substituents, i.e. aryl groups, preferably substituted with one aryl group.

As used herein, the term "aryl group" denotes an aromatic group which may or may not contain heteroatoms like nitrogen, oxygen or sulfur. Aryl groups which do not contain heteroatoms are preferred. Preferred aryl groups comprise up to 20 carbon atoms, more preferably up to 12 carbon atoms, for example, 10 or 6 carbon atoms. Preferred embodiments of aryl groups are phenyl and naphthyl, especially phenyl. Further, the aryl group may optionally be substituted by one or more, more preferably one or two, substituents. Preferably, the aryl group is substituted at the meta or para position, most preferably at the para position. Suitable substituents include halo alkyl, e.g. trifluoromethyl, dichloroethyl and the like, alkoxy, preferably alkoxy groups containing 1 to 6 carbon atoms like methoxy or ethoxy, halo, e.g. iodo, bromo, chloro or fluoro, preferably chloro and fluoro, nitro and $C_{1-6}$ alkyl, preferably $C_{1-4}$ alkyl such as methyl, ethyl, n-propyl, isopropyl, n-butyl, iso-butyl and t-butyl. Preferred $C_{1-6}$ alkyl groups include methyl, isopropyl and t-butyl, particularly methyl. Particularly preferred aryl substituents are chloro and nitro. However, still more preferably the aryl group is unsubstituted.

Preferred such aryl substituted $R^1$ groups are benzyl, 4-isopropylbenzyl, 4-methylbenzyl, 2-methylbenzyl, 3-methylbenzyl, 4-[t-butyl]benzyl, 4-[trifluoromethyl]benzyl, 4-methoxybenzyl, 3,4-[di-chloro]benzyl, 4-chlorobenzyl, 4-fluorobenzyl, 2-fluorobenzyl, 3-fluorobenzyl, 2,3,4,5,6-pentafluorobenzyl 3-nitrobenzyl, 4-nitrobenzyl, 2-phenylethyl, 4-phenylbutyl, 3-pyridinyl-methyl, 4-diphenyl-methyl and benzyl-5-[(1-acetyloxyethoxy)-carbonyl]. More preferred such R1 groups are benzyl, 4-isopropylbenzyl, 4-methylbenzyl 4-nitrobenzyl and 4-chlorobenzyl. Most preferred is benzyl.

If $R^1$ is a substituted alkyl group, one or more oxo substituents are preferred. Preferably, such groups substituted alkyl groups are straight-chained $C_{4-12}$ alkyl groups which are substituted by one, two or three oxo groups. Examples of such groups include 3,6-dioxa-1-octyl and 3,6,9-trioxa-1-decyl. In another preferred embodiment, $R^1$ is an alkyl group interrupted by one or more oxygen atoms (ether or polyether group), preferably a straight-chained $C_{4-12}$ alkyl and more preferably a straight-chained $C_{6-10}$ alkyl group being interrupted by 1 to 4 oxygen atoms, more preferably a straight-chained polyethylene glycol group (—$(CH_2)_2$—O—)n with n being an integer of from 1 to 5.

If $R^1$ is an unsubstituted alkyl group, $R^1$ groups that are saturated straight-chained or branched alkyl groups are preferred. If $R^1$ is a saturated straight-chained alkyl group, $C_{1-10}$ straight-chained alkyl group are preferred. Representative examples of suitable straight-chained alkyl groups include methyl, ethyl, n-propyl, n-butyl, n-pentyl, n-hexyl and n-octyl. Particularly preferred are $C_{1-6}$ straight-chained alkyl group, most particularly preferred are methyl and n-hexyl. If $R^1$ is a saturated branched alkyl group, such branched alkyl groups preferably consist of a stem of 4 to 8, preferably 5 to 8 straight-chained carbon atoms and said stem is branched by one or more $C_{1-6}$ alkyl groups, preferably $C_{1-2}$ alkyl groups. Examples of such saturated branched alkyl groups include 2-methylpentyl, 4-methylpentyl, 1-ethylbutyl and 3,3-dimethyl-1-butyl.

In compounds of formula I, each $R^2$ independently represents a hydrogen atom or a group $R^1$. Particularly preferred for use in the invention are those compounds of formula I in which at least one $R^2$ represents a hydrogen atom. In especially preferred compounds each $R^2$ represents a hydrogen atom.

Preferably, compounds of formula I and skin compatible salts thereof are used in the compositions of the invention, wherein $R^1$ is $C_1$-$C_{10}$-alkyl, more preferably $C_1$-$C_8$-alkyl and even more preferably $C_1$-$C_6$-alkyl; and both $R^2$ represent hydrogen. In a preferred embodiment, $R^1$ is straight chained $C_1$-$C_{10}$-alkyl, more preferably straight chained $C_1$-$C_8$-alkyl and even more preferably straight chained $C_1$-$C_6$-alkyl; and both $R^2$ represent hydrogen. One of the most preferred compounds of formula I is 5-ALA hexyl ester and skin compatible salts thereof, preferably the HCl salt or a sulfonate salt (salt of sulfonic acid or a sulfonic acid derivative).

5-ALA esters and skin compatible salts thereof for use in the composition of the invention may be prepared by any conventional procedure available in the art, e.g. as described in WO 96/28412, WO 02/10120, WO 2003/041673 and WO 2009/077960. Briefly, 5-ALA esters may be prepared by reaction of 5-ALA with the appropriate alcohol in the presence of a catalyst, e.g. an acid. Alternatively, compounds for use in the invention like 5-ALA methyl ester or 5-ALA hexyl ester may be available commercially, e.g. from Photocure ASA, Norway The preparation of skin compatible salts of 5-ALA esters is known in the art, e.g. described in WO 2005/092838. Briefly, skin compatible salts of 5-ALA esters may be prepared by reaction of a skin compatible 5-ALA salt, e.g. 5-ALA hydrochloride with the appropriate alcohol.

The 5-ALA esters for use in the composition of the invention may be in the form of a free amine, e.g. —$NH_2$, —$NHR^2$ or —$NR^2R^2$ or preferably in the form of a skin compatible salt. Such salts are preferably acid addition salts of organic or inorganic acids, preferably strong organic or inorganic acids. Suitable acids include, for example, hydrochloric acid, nitric acid, hydrobromic acid, phosphoric acid, phosphoric acid derivatives, sulfuric acid, sulfonic acid and sulfonic acid derivatives which are described in WO 2005/092838, the entire content of which is incorporated herein by reference. A preferred acid is hydrochloric acid, HCl. Procedures for salt formation are conventional in the art and for instance described in WO 2005/092838.

The desired amount of the derivative of 5-ALA or skin compatible salts thereof in the composition according to the invention will be dependent on several factors, including the specific nature of the formulation, whether or not a light source is used in the treatment and if so, the type of light source and the selected wavelength, the duration of the treatment and the overall number of treatments. Taking into account these various factors, the amount may readily be determined by those skilled in the art. The composition according to the invention comprises 2% by weight or less of the derivative of 5-ALA or skin compatible salts thereof, preferably 0.02 to 1.75% by weight, more preferably 0.05 to 1.5% by weight, e.g. 0.5 to 1.25% by weight and most preferably 0.1 to 1.0% by weight with the range of 0.25 to 0.75% by weight being the most preferred one. In determining the desired amount within these ranges, the following criteria within the knowledge and expertise of those skilled in the art may also be considered:

compositions which are capable of penetrating more deeply into the skin e.g. due to the nature of the composition, the nature of the selected 5-ALA derivative or due to the presence of agents which promote deeper penetration, e.g. skin penetration enhancing agents, will typically contain a lower concentration of 5-ALA derivatives or skin compatible salts thereof than compositions which tend to remain primarily on the surface of the skin;

compositions intended for longer durations of skin treatment (i.e. longer incubation of the composition on the skin and/or longer illumination) normally contain less 5-ALA derivative or skin compatible salts thereof than compositions intended for shorter durations of treatment;

compositions intended for more than one course of skin treatment, e.g. several or many treatments such as several treatments over a period or repeated treatments, normally contain less 5-ALA derivative or skin compatible salts thereof than compositions intended for use once or intended for use a limited number of times, often with a delay between each treatment;

compositions intended for the treatment of skin with only few signs of (photo)aging may contain less 5-ALA derivative or skin compatible salts thereof than compositions intended for treatment of severely (photo)aged skin.

The compositions according to the invention are topically applied to the skin and are skin compatible, i.e. generally non-irritant and well-tolerated.

The composition according to the invention further comprises 70% or more by weight of water. In a preferred embodiment, the composition according to the invention comprises 75% or more by weight of water, more preferably 80% or more by weight of water. The relatively high water content compared to the amount of lipid carrier ensures a quick absorption of the 5-ALA derivative or the skin compatible salt thereof into the skin, resulting in a short incubation time, i.e. the time period starting with the application of the composition to the skin to the point in time where the illumination with light commences. A short incubation time is favored by consumers and cosmeticians/dermatologists. If the composition according to the invention is intended to be in the form of a cream, such cosmetic composition preferably comprises 75% or more by weight of water, more preferably 80% or more by weight of water. If the cosmetic composition according to the invention is intended to be in the form of a lotion, such cosmetic composition preferably comprises 80% or more by weight of water, more preferably 85% or more by weight of water.

Despite its high water content, the compositions according to the invention are stable at room temperature and keep their appearance and texture, thus providing an adequate shelf life for e.g. use as a commercial cosmetic product. This stability is surprising since it is well known in the art that the presence of water in compositions containing 5-ALA esters leads to degradation of said esters. As a consequence, compositions comprising 5-ALA esters are either stored in cool conditions or are prepared immediately before use. As an example, Metvix®, a cream containing the hydrochloride salt of 5-ALA methyl ester is stored in cold conditions. Hexvix® (Photocure ASA), a diagnostic agent for the detection of bladder cancer, is an aqueous solution which comprises the hydrochloride salt of 5-ALA hexyl ester. Hexvix® is supplied as a lyophilized powder and dissolved in an aqueous solvent immediately before use.

The composition according to the invention further comprises 2-25% by weight of at least one lipid carrier. The term "lipid carrier" denotes a carrier which is generally soluble in organic solvents and largely insoluble in water. In a preferred embodiment, the lipid carrier according to the invention is a fat, wax, oil, free fatty acid or an ester of a fatty acid or a fatty alcohol.

Said lipid carrier is generally a skin compatible lipid carrier, i.e. a lipid carrier which is compatible with the human skin, but preferably also with mucous membranes, nails and/or hair and which is usually non-irritant and well-tolerated: Preferred lipid carriers are those which are commonly used in dermal compositions, e.g. in pharmaceutical or cosmetic preparations for use on the skin.

The term "at least one" means that the composition according to the invention contains one lipid carrier or several different lipid carriers. The composition according to the invention may contain several lipid carriers of the same type or of a different type, e.g. several different fats or a fat and a wax. By way of example, the composition may comprise as lipid carriers tricaprylin and caprylic/capric triglyceride, i.e. two different fats. Further, by way of example the composition may comprise as lipid carriers tricaprylin and stearic acid, i.e. a fat and a fatty acid.

The composition according to the invention may comprise as a lipid carrier one or more fats. Fats are triglycerides, i.e. triesters of one molecule glycerol and 3 molecules fatty acids. The 3 fatty acids may be identical or different fatty acids.

The fats used in the composition according to the invention may be solid or liquid (i.e. oils) at room temperature, i.e. at temperatures of about 18° C. to about 25° C. The fats may be synthetic, semi-synthetic or of animal or vegetable origin.

In a preferred embodiment, the lipid carrier according to the invention is a fat, preferably a triglyceride of glycerol and 3 identical or different, preferably identical, saturated and/or unsaturated, branched and/or unbranched fatty acids with a chain length of from 6 to 24, in particular 8 to 18 carbon atoms. Preferred fats are tricaprylin, trihydroxystearin, tricaproin, triheptanoin, caprylic/capric triglyceride, caprylic/capric/linoleic triglyceride, caprylic/capric/lauric triglyceride, caprylic/capric/myristic/stearic triglyceride and caprylic/capric/succinic triglyceride, Some of these fats are marketed under the name "Miglyol®" (Sasol, Witten, Germany), e.g. Miglyol® 812 which is caprylic/capric triglyceride and a preferred fat according to the invention.

Other preferred fats are natural oils of animal or vegetable origin or are fractions of said oils, such as safflower oil, soybean oil, palm oil, avocado oil, palm kernel oil, corn oil, cotton seed oil, arctium lappa seed oil, canola oil, borgo officialis seed oil, brassica campestris oleifera oil, brevoortia oil, bubulum oil, cistus ladaniferus oil, elaeis guineensis oil, coconut oil, sunflower oil, castor oil, pine oil, olive oil, peanut oil, almond oil, wheat germ oil, grape seed oil, thistle oil, evening primrose oil, cocoa butter, lard, tallow, and palm olein. Further examples of fats are illipe butter, shea butter, cocoa butter, kokum butter, sal butter, lecithin, japan wax and other natural oils or fractions thereof. Other examples of fats include hydrogenated or partially hydrogenated oil selected from partially or fully hydrogenated soybean oil, rapeseed oil, cotton seed oil, sunflower oil, castor oil, coconut oil and fractions thereof. The fats may be synthetic or semi-synthetic, such as medium-chain triglycerides (MCT).

The fats used in the invention may be prepared using standard processes and procedures well-known in the art, although many are commercially available from various manufacturers such like Sasol, Croda, Cognis, Gattefossé and others.

The composition according to the invention may comprise as a lipid carrier one or more waxes. Chemically, waxes are a type of lipid that may contain a wide variety of long-chain alkanes, esters, polyesters and hydroxy esters of long-chain primary alcohols and fatty acids. They are usually distinguished from fats by the lack of triglyceride. Natural waxes such as animal or plant waxes are usually mixtures of several components, including wax esters, wax acids, wax alcohols, and hydrocarbons while synthetic waxes, especially petroleum derived waxes are usually hydrocarbons.

The waxes used in the composition according to the invention may be solid or liquid at room temperature, i.e. at temperatures of about 18° C. to about 25° C. The waxes may be synthetic, semi-synthetic or of animal or vegetable origin.

Preferred waxes are chosen from the group of vegetable waxes, animal waxes, mineral waxes and petrochemical waxes. According to the invention, preferred waxes are candelilla wax, carnauba wax, lanolin (wool wax), wool wax alcohol, esparto grass wax, cork wax, guaruma wax, rice bran wax, sugar cane wax, berry wax, ouricury wax, jojoba oil, soy wax, beeswax, uropygial grease, ceresine, paraffin waxes and micro waxes. Also chemically modified waxes or synthetic waxes may be used in the invention, such as for instance those available under the trade names Synchrowax HRC (glycerol tribehenate), and Synchrowax AW 1C ($C_{18-36}$-fatty acid) from Croda GmbH, and also montan ester waxes, sasol waxes, hydrogenated jojoba oil, synthetic or modified beeswaxes (e.g. dimethicone copolyol beeswax and/or $C_{30}$-$C_{50}$-alkyl beeswax), polyalkylene waxes and polyethylene glycol waxes.

The composition according to the invention may comprise as a lipid carrier one or more oils. Oils useful in the composition of the invention are mineral oils (liquid petrolatum jelly), oils of animal or vegetable origin and semi-synthetic or synthetic oils.

Oils of animal or vegetable origin often are liquid fats or contain triglycerides of glycerol and fatty acids, i.e. fats, as their major component. Hence some of the following mentioned oils have also been discussed earlier under the term "fat".

Preferred oils of animal and/or vegetable origin for use in the invention are safflower oil, soybean oil, palm oil, avocado oil, palm kernel oil, corn oil, cotton seed oil, arctium lappa seed oil, canola oil, borgo officialis seed oil, brassica campestris oleifera oil, brevoortia oil, bubulum oil, cistus ladaniferus oil, elaeis guineensis oil, coconut oil, sunflower oil, castor oil, pine oil, olive oil, peanut oil, almond oil, wheat germ oil, grape seed oil, thistle oil, evening primrose oil and the like.

Preferred mineral oils are paraffin oils like higher viscosity paraffin oil (paraffinum liquidum) and lower viscosity paraffin oil (paraffinum perliquidum).

Preferred semi-synthetic oils are those extracted from natural oils of vegetable or animal origin or extracted from botanic sources. They may be chemically modified. A preferred example is squalene, a compound that may be obtained from shark liver oil, amaranth seed, rice bran, wheat germ or olives. It may be chemically modified, e.g. hydrogenated (perhydrosqualene). Preferred synthetic oils are fluoro oils like perfluoropolyethers.

The free fatty acids used in the composition according to the invention may be solid or liquid at room temperature, i.e. at temperatures of about 18° C. to about 25° C. Preferred free fatty acids are saturated and/or unsaturated, branched and/or unbranched fatty acids with a chain length of from 3 to 30 carbon atoms, more preferably a chain length of from 12 to 30 carbon atoms and most preferably a chain length of from 18 to 26 carbon atoms, such as palmitic acid, stearic acid, erucic acid, oleic acid, linoleic acid, arachidonic acid and behenic acid.

The esters of fatty acids used in the composition according to the invention are preferably esters of fatty acids that are saturated and/or unsaturated, branched and/or unbranched fatty acids with a chain length of from 3 to 30 carbon atoms with straight-chain or branched mono-, di- or polyalcohols with a low number of carbon atoms like 3 to 9 carbon atoms, preferably isopropanol, n-butanol, hexanol, n-octanol, isooctanol, ethylhexanol, isononanol, propylene glycol and glycerol. The esters of fatty alcohols used in the composition according to the invention are preferably esters of fatty alcohols that are saturated and/or unsaturated, branched and/or unbranched fatty alcohols with a chain length of from 3 to 30 carbon atoms with straight-chain or branched mono-, di- or polycarboxylic acids with a low number of carbon atoms like 3 to 9 carbon atoms. Suitable examples of such esters of fatty acids or fatty alcohols are isopropyl palmitate, isopropyl stearate, n-butyl stearate, glyceryl stearate, n-hexyl laurate, isooctyl stearate, isononyl stearate, isononyl isononanoate, 2-ethylhexyl palmitate, 2-hexyldecyl stearate and 2-octyldodecyl palmitate.

Preferred lipid carriers for use in the composition according to the invention are fats, more preferably triglycerides of glycerol and 3 identical or different saturated and/or unsaturated, branched and/or unbranched fatty acids with a chain length of from 6 to 24, in particular 8 to 18 carbon atoms. Most preferred lipid carriers for use in the composition according to the invention are tricaprylin, trihydroxystearin, tricaproin, triheptanoin, caprylic/capric/coco glycerides, caprylic/capric glycerides, caprylic/capric triglyceride, caprylic/capric/linoleic triglyceride, caprylic/capric/stearic trygliceride, caprylic/capric/lauric triglyceride, caprylic/capric/myristic/stearic triglyceride and caprylic/capric/succinic triglyceride.

The at least one lipid carrier is present in the composition according to the invention in a proportion ranging from 2 to 25% by weight, preferably from 2.5 to 20% by weight and more preferably from 5.0 to 15% by weight.

The compositions according to the invention comprise one or more emulsifiers, i.e. the composition according to the invention is an emulsion. The term "emulsifier" includes emulsifying agents, co-emulsifiers and agents with surfactant properties. The term "one or more" means that the composition according to the invention comprises one emulsifier or several different emulsifiers.

The composition according to the invention is preferably an oil-in-water (O/W) emulsion. O/W emulsions always have a pseudoplastic flow behavior which makes it easier for the consumer or the cosmetician/dermatologist to apply such products to the skin, i.e. such O/W emulsions have a texture which is preferred by the consumer.

Thus, viewed from a second aspect the invention provides a composition which is an oil-in-water emulsion, said composition comprises
 a) 2% by weight or less of 5-ALA, a derivative of 5-ALA or skin compatible salts thereof
 b) 70% by weight or more of water;
 c) 2-25% by weight of at least one lipid carrier; and
 d) one or more oil-in-water emulsifiers.

In a preferred embodiment, the size of the emulsified particles is in average >200 nm, preferably >500 nm, i.e. the composition is not a nanoemulsion or microemulsion.

Thus, viewed from a third aspect the invention provides a composition which is an oil-in-water emulsion wherein the size of the emulsified particles is in average >200 nm, preferably >500 nm, said composition comprises
 a) 2% by weight or less of 5-ALA, a derivative of 5-ALA or skin compatible salts thereof
 b) 70% by weight or more of water;
 c) 2-25% by weight of at least one lipid carrier; and
 d) one or more oil-in-water emulsifiers.

The composition according to the invention may be more or less fluid, e.g. an emulsion of the liquid, semi-liquid, soft or semi-solid consistency. It may have the appearance of a gel, cream, lotion, milk or liquid. Lotions and creams are preferred.

The one or more emulsifiers used in the composition of the invention may be any of the usual type of emulsifiers used for the preparation of compositions for use on the mammal skin, preferably for use on the human skin. In a preferred embodiment, the one or more emulsifiers used in the composition of the invention may be any of the usual type of emulsifiers used for the preparation of O/W emulsions for use on the mammal, preferably human, skin. Such emulsifiers are e.g. non-ionic-, cationic-, anionic and betaine compounds with the non-ionic emulsifiers being high HLB emulsifiers, preferably emulsifiers with an HLB value of 8 to 18. The use of non-ionic or cationic emulsifiers is preferred, more preferred is the combined use of non-ionic and cationic emulsifiers, preferably the combined use of non-ionic emulsifiers with an HLB value of 8 to 18 and cationic emulsifiers.

The emulsifiers used in the composition according to the invention can be synthetic, semi-synthetic or natural compounds. Some specific examples of such compounds are: almondamidopropyl betaine, aminoethyl sulfate, 3-aminopropane sulfonic acid, alkyl sulfate salts, e.g. ammonium salts and other salts, ethoxylated alcohols (pareths), cholesterol esters, calcium lignosulfonate and other calcium sulfonic acid salts, calcium myristate and other calcium fatty acid salts, capric acid, capronic acid, capryleth carboxylic acids, polyoxyethylene ethers (ceteareths), e.g. ceteareth-20, PEG alkyl ethers (ceteths), ethoxylated unsaturated alcohols (cetoleths), fatty alcohols, e.g. cetyl alcohol, stearyl alcohol or mixtures thereof (cetearyl alcohol), ethoxylated docosanol (beheneths) and behentrimonium salts like behentrimonium methosulfate, ethoxylated cholesterol derivatives (choleths), cocamine and cocamides, emulsifying wax, diethanolamine alkyl sulfates, DEA-oleth-3 phosphate and similar phosphates, deceths and deceths phosphates, dextrin laurate and other dextrin fatty acid esters, disodium oleyl sulfosuccinate and other sulfosuccinate compounds, dodoxynols, glucereth stearate, glycereth phosphate, quaternary ammonium compounds, glyceride citrates and phosphates, hydroxycetyl phosphate, isosteareths, ethoxylated lanolin alcohols (laneths), lanolin and lanolin derivatives, laurylamides, ethoxylated dodecanol (laureths) and lauryltrimonium salts, magnesium laureth sulfates, meroxapols, methyl glucose laurate, methyl laurate, nonoxynols, octoxynols, octyldodeceths, oleths, palmamides, fatty esters of polyethylene glycol (PEG) such as PEG-100 stearate, PEG 50-stearate and PEG 40-stearate, PEG amines, ethoxylated castor oil and other ethoxylated oils and hydrophobic compounds, polyoxamers, poloxamines, polyglyceryl-2-distrearate and other esters, steareths and sorbeths, polysorbates (Tween) and esters of sorbitan (Span).

In a preferred embodiment, non-ionic- and/or cationic emulsifiers are used, in a more preferred embodiment non-ionic and cationic emulsifiers are used and in a most preferred embodiment, non-ionic emulsifiers with an HLB value of 8 to 18 and cationic emulsifiers are used.

Preferred non-ionic emulsifiers are polysorbates, polyoxyethylene ethers (ceteareths), e.g. ceteareth 20, fatty alcohols, e.g. cetyl alcohol, stearyl alcohol or mixtures thereof (cetearyl alcohol).

Preferred cationic emulsifiers are quaternary ammonium salts such as behenyl-, lauryl-, cet-, or stearyltrimonium salts, preferably behentrimonium salts like behentrimonium methosulfate or behentrimonium chloride.

In another preferred embodiment, the mixing ratio of non-ionic and cationic emulsifier is in the range of 1:1 or the amount of non-ionic emulsifiers (in % by weight) in the composition according to the invention is greater than the amount of cationic emulsifier.

The one or more emulsifiers are present in the composition according to the invention in a proportion ranging from 0.5 to 20% by weight, preferably from 1 to 15% by weight and more preferably from 2 to 12% by weight.

The compositions according to the invention may further comprise one or more dermal adjuvants, i.e. adjuvants which are commonly used in compositions for use on the skin, e.g. preserving agents, antimicrobial agents, fragrances, coloring agents, colorants, dyestuffs, fillers, pigments, antioxidants, solvents, viscosity modifiers (e.g. thickening agents) and/or pH-adjusters/modifiers. Dermal adjuvants are known in the art and dermal adjuvants conventionally used in cosmetic and pharmaceutical dermal products may be used in the compositions of the invention. Such dermal adjuvants may be used in the composition of the invention an amount which is conventionally used in cosmetic and pharmaceutical dermal products. Said amount can vary, for example, from approximately 0.01 to 10% by weight, preferably from 0.1 to 5% by weight.

Further, the composition according to the invention may comprise one or more cosmetic or dermatological agents such as proteins or hydrolysates thereof, peptides, amino acids, sugars, urea, allantoin, hyaluronic acid, urea, alpha- and/or beta-hydroxy acids, vitamins or derivatives thereof, retinoids, ceramides or plant extracts. These various cosmetic or dermatological agents are typically used in concentrations of from approximately 0 to 10% by weight, preferably from 0 to 5% by weight.

Moreover, the composition according to the invention may comprise one or more surface penetration enhancers. Suitable surface penetration enhancers are chelating agents such as aminopolycarboxylic acids, for example EDTA, CDTA (cyclohexane diamine tetraacetic acid), DTPA and DOTA and well known derivatives/analogues thereof. EDTA and DTPA are particularly preferred. Where present, the chelating agent may conveniently be used at a concentration of 0.05 to 20%, e.g. 0.1 to 10% by weight. Other surface penetration enhancers such as dialkylsulfoxides, e.g. dimethylsulfoxide (DMSO), surfactants, bile salts and fatty acids (e.g. oleic acid) may also be present. Examples of appropriate surface penetrating assisting agents include isopropanol, DMSO and other dialkylsulfoxides, in particular n-decylmethyl-sulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 1986, 5: 167-177), and Azone® (Stoughton et al., Drug Dpv. Ind. Pharm. 1983, 9: 725-744), or mixtures thereof. The surface penetration agent may conveniently be provided in a concentration range of 0.2 to 20% by weight, e.g. about 1 to 10% by weight.

As mentioned above, such surface penetration enhancers may be included in the compositions according to the invention. Alternatively, they may be co-administered, e.g. applied before or after the composition has been administered to the skin.

The pH of the compositions according to the invention is preferably maintained in a range of from 4 to 6, more preferably in a range of from 4 to 5. This can be achieved by the use of suitable pH modifiers, e.g. buffering agents or any component which directly or indirectly maintains the pH. Suitable buffering agents are those which are commonly used in dermal products, i.e. pharmaceutical or cosmetic products, e.g. buffering agents that can be found in the International Nomenclature of Cosmetics (INCI) listing.

The compositions according to the invention exhibit excellent shelf life, which may be further enhanced by minimizing, e.g. excluding the presence of any component which either directly or indirectly reacts with or otherwise might catalyze the degradation of the derivative of 5-ALA. Such components include, for example, metal compounds such as iron compounds. Ideally, such components will be absent from the compositions herein described. However, where present, their amount should be minimal, e.g. less than 0.5% by weight, preferably less than 0.3% by weight, more preferably less than 0.1% by weight. The compositions will preferably be substantially free from any iron compound.

The compositions according to the invention will generally be prepared by simple mixing of the components.

In a preferred embodiment, a water phase A and a lipid phase B are combined at room temperature. In case of solid or semi-solid components, i.e. lipids or emulsifiers or adjuvants etc., phase A and the lipid phase B are combined at an elevated temperature, preferably at 70 to 90° C. or more preferably at 75 to 85° C., in order to melt said solid or semi-solid components. In an alternative and more preferred embodiment, phase A and phase B are each heated to an elevated temperature, preferably at 70 to 90° C. or more preferably at 75 to 85° C., and then combined. Combining phase A and B is conveniently promoted by mixing and/or agitation. The lipid phase B contains the lipid carrier and preferably the one or more emulsifiers. Suitably, the lipid phase B may further contain such adjuvants or cosmetic or dermatological agents which are miscible, dispersible or dissolvable in said lipid phase. The water phase A contains water and may further contain such adjuvants or cosmetic or dermatological agents which are miscible, dispersible or dissolvable in said water phase. The water phase A may further contain the derivative of 5-ALA or the skin compatible salt thereof. In another and preferred embodiment, the derivative of 5-ALA or the skin compatible salt thereof is added as a solid to a combined and optionally cooled phase A and B. Optional adjuvants or cosmetic or dermatological agents are preferably also added to a combined and optionally cooled phase A and B.

In another preferred embodiment, a lipid phase D and a phase C are combined at room temperature. The lipid phase D preferably contains the lipid carrier or only a part thereof, and the derivative of 5-ALA or the skin compatible salt thereof. Phase C contains the remainder of the composition. In order to prepare phase C, a water phase A is prepared as described above, containing the components as described above. Said water phase A is combined with a lipid phase B* which contains no lipid carrier or only a part thereof, and preferably the one or more emulsifiers. Suitably, the lipid phase B* may further contain such adjuvants or cosmetic or dermatological agents which are miscible, dispersible or dissolvable in said lipid phase B*. In case of solid or semi-solid components, phase A and phase B* are preferably each heated to an elevated temperature, preferably at 70 to 90° C. or more preferably at 75 to 85° C., and then combined. For preparing phase C, phase A and B* are conveniently mixed or agitated.

The composition according to the invention is conveniently provided in a container commonly used for dermal products such as tubes, jars, bottles, boxes, pots, dispensers etc. and such containers contain multiple "doses" of the composition, i.e. an amount of the composition which is sufficient for multiple applications to the skin. Alternatively, and preferably, the composition may be provided in single "doses", i.e. in sachets, small tubes, blister packs or bottles etc. containing an amount of the composition which is suitable for a single application to the skin. The composition preferably has a long shelf-life at room temperature, i.e. showing no change in appearance such as discoloration or separation of the components (disintegration) over a period of at least 1 month, preferably at least 6 month, more preferably 1 year and even more preferably over a period of up to 2 years.

In another preferred embodiment, components of the composition and/or mixtures of several components are filled in a multiple compartment container and the composition is prepared in situ before being used on the skin by combining and mixing the various components or mixtures thereof. In a further preferred embodiment, said multiple compartment container contains a single "dose" of the composition, i.e. an amount which is suitable for a single application to the skin. The use of multiple compartment containers results in a particularly long the shelf-life of the product at room temperature.

In one such embodiment, the multiple compartment container is a two-compartment container containing a first compartment with the derivative of 5-ALA or the skin compatible salt thereof as a dry, solid compound and a second compartment with the remainder of the composition, i.e. water, the at least one lipid carrier, one or more emulsifiers and optionally adjuvants, cosmetic or dermatological agents or surface penetration enhancers. In another such embodiment, the multiple compartment container is a two-compartment container containing a first compartment with the derivative of 5-ALA or the skin compatible salt thereof dissolved, dispersed or mixed with the at least one lipid carrier and optionally the one or more emulsifiers and a second compartment containing water and optionally the one or more emulsifiers. Any adjuvant, cosmetic or dermatological agent or surface penetration enhancer which is present in the final composition according to the invention is contained in the compartment wherein said adjuvant, cosmetic or dermatological agent or surface penetration enhancer fits best in terms of stability, miscibility and compatibility with other components contained in said compartment. In a preferred embodiment, the multiple compartment container is a two-compartment container containing a first compartment with the derivative of 5-ALA or the skin compatible salt thereof dissolved, dispersed or mixed with the at least one lipid carrier and a second compartment containing the remainder of the composition, i.e. water, one or more emulsifiers and optionally adjuvants, cosmetic or dermatological agents or surface penetration enhancers.

In another such preferred embodiment, the multiple compartment container is a three-compartment container containing a first compartment with the derivative of 5-ALA or the skin compatible salt thereof as a dry, solid compound, a second compartment containing the at least one lipid carrier and optionally but preferably one or more emulsifiers and a third compartment containing water and optionally, but not preferred one or more emulsifiers. Again, any adjuvant, cosmetic or dermatological agent or surface penetration enhancer which is present in the final composition according to the invention is contained in the compartment wherein said adjuvant, cosmetic or dermatological agent or surface penetration enhancer fits best in terms of stability, miscibility and compatibility with other components contained in said compartment.

In one embodiment, the content of the various compartments of a multiple compartment container are mixed together outside the container, e.g. by pouring the content from said container into a bowl or jar and mixing it, e.g. with the help of a spatula or the like. In a preferred embodiment, the content of the various compartments of a multiple compartment container are mixed together inside of the container with the container being intact. This can be done by for instance having frangible seals which separate the compartments from each other, e.g. by choosing a material for the seals which is breakable, e.g. upon exerting pressure on such a seal. The material of the container which separates the content from the outside environment should of course not be breakable. In a preferred embodiment a colorant (color additive) or dyestuff is added to one of the compartments. Such colorant or dyestuff works as a visual indicator for the consumer to determine proper mixing of the contents of the container before applying the so-mixed composition to the skin. In a preferred embodiment, the container is marketed as a product comprising the container and a package insert with instructions. Said package insert preferably contains a color scale which shows the color of a properly mixed composition and thus enables the consumer to determine whether or not his/her composition is properly mixed. Colorants and dyestuffs which can be used in compositions are such that are compatible with the components of the composition according to the invention and which are generally used in dermal products such as pharmaceutical or cosmetic dermal products. Such colorants and dyestuffs are known in the art and e.g. include the color additives with are listed in 21 C.F.R. parts 73 and 74. The container may include a dispenser end piece with a removable cap which allows the dispensing of the final composition from the container. Alternatively, the container may include a foil which seals the compartments from the outside environment and which may be removed after the content of the compartments have been mixed together inside the container.

Another aspect of the invention is a container comprising a first and a second compartment wherein said first compartment comprises a derivative of 5-ALA or skin compatible salts thereof and at least one lipid carrier and said second compartment comprises water, one or more emulsifiers and optionally at least one lipid carrier, and wherein the composition according to the invention is obtained by mixing the contents of said first and second compartment, preferably mixing the contents of said first and second compartment inside the container with the container remaining intact.

Thus, in another aspect the invention provides a container comprising a first and a second compartment wherein said first compartment comprises a derivative of 5-ALA or skin compatible salts thereof and at least one lipid carrier and said second compartment comprises water, one or more emulsifiers and optionally at least one lipid carrier, and wherein the composition obtained by mixing the contents of said first and second compartment comprises a) 2% by weight or less of said derivative of 5-ALA or said skin compatible salts thereof
b) 70% by weight or more of said water;
c) 2-25% by weight of said at least one lipid carrier; and
d) said one or more emulsifiers.

In a preferred embodiment, the at least one lipid carrier in said first and optionally in said second compartment are identical.

The first and/or the second compartment of the container according to the invention may further comprise one or more dermal adjuvants such as preserving agents, antimicrobial agents, fragrances, coloring agents, colorants, dyestuffs, fillers, pigments, antioxidants, solvents, viscosity modifiers and/or pH-adjusters/modifiers as described earlier.

Further, the first and/or the second compartment of the container according to the invention may comprise one or more cosmetic or dermatological agents such as proteins or hydrolysates thereof, peptide, amino acids, sugars, urea, allantoin, hyaluronic acid, urea, alpha- and/or beta-hydroxy acids, vitamins or derivatives thereof, retinoids, ceramides or plant extracts as described earlier.

Moreover, the first and/or the second compartment of the container according to the invention may comprise one or more surface penetration enhancers as described earlier.

In a preferred embodiment, only the second compartment of the container according to the invention may comprise one or more dermal adjuvants and/or one or more cosmetic or dermatological agents and/or one or more surface penetration enhancers.

The composition according to the invention is applied to the subject's skin, preferably to a human person's skin. The composition is preferably applied to the face, but may also be applied to other areas such as the neck, chest, arms, legs or the hands. Depending on the viscosity of the composition, this can be done by using the fingers. Alternatively, any applicator known for use in applying dermal products, e.g. a spray, a pad or a spatula, may be used. The subject's skin is preferably cleaned before applying the composition according to the invention, e.g. by washing it with soap followed by thorough rinse with water.

The compositions of the invention are generally intended to be used in conjunction with illumination, i.e. exposure to light, sufficient to achieve the desired cosmetic effect. The term "light treatment" is used herein in its most general sense to refer to illumination of the target skin surface of the subject, i.e. exposure of said target skin surface to light.

Whilst light treatment may be effected using a specific or common artificial light source, it can also be achieved by exposure to natural light sources such as daylight or sunlight; due to its ready availability, the use of natural light sources or any light source which provides artificial sunlight, i.e. the entire range from UV to IR, represents a particularly preferred aspect of the invention. Since the intensity of natural daylight or sunlight may vary during the illumination period, if necessary, the light dose received by a subject from natural daylight or sunlight can easily be monitored by way of portable photometers, which are commercially available from for instance International Light Technologies. These photometers monitor the total light dose and give a signal to the user when the desired light dose has been reached.

Specific artificial light sources which may be used are well known in the art and include common lamps for dermatological light treatments, e.g. LED lamp systems, lasers and intense pulsed light. Using such specific artificial light sources, the wavelength of light used for illumination may be selected to achieve a more efficacious cosmetic treatment effect. The most effective light is light in the wavelength range of 300-800 nm, typically of 400-700 nm. Penetration of light into tissues depends on the wavelength used and is deeper for red light than for blue light. Wavelengths in the red light region, e.g. 630 to 690 nm, and wavelengths in the blue light region, e.g. 390 to 490 nm are particularly suitable.

Light treatment with common artificial light sources is a preferred embodiment and normal home or office lights may be used.

During light treatment, light will in general be applied at a dose level of 0.1 to 100 $J/cm^2$, preferably 5 to 50 $J/cm^2$, more preferably 10 to 40 $J/cm^2$. An irradiance (light intensity) of 3 to 100 $mW/cm^2$ may be used, preferably of 5 to 80 $mW/cm^2$ and more preferably of 10 to 70 $mW/cm^2$.

The duration of illumination will depend on various factors, including the nature and concentration of the derivative of 5-ALA or the skin compatible salt thereof, the nature of the composition according to the invention, the light source, (light dose and irradiance) and severity of the aging of the skin. Illumination with specific artificial light sources is preferably performed for about 5 to 60 minutes, more preferably for about 5 to 30 minutes and most preferably 7.5 to 15 minutes. A single illumination from a specific artificial light source is preferably be used; alternatively, a light split dose in which the light dose is delivered in a number of fractions, e.g. 1 to 10 minutes between illuminations, may be used. During illumination of the facial skin with a specific artificial light source, e.g. a laser or LED lamp system, it may be preferred that the subject wears suitable eye-protection, e.g. goggles. If illumination is carried out by exposure to natural light or common artificial light, the treated skin area is exposed to said natural light or common artificial light for preferably 2 to 4 hours, e.g. 2.5 to 3 hours.

The composition is administered to the subject's skin and a certain time period may be allowed to elapse before the skin to be treated is exposed to light to achieve the desired cosmetic effect. Before exposure to light, the composition may be removed from the skin, e.g. by washing the skin with soap followed by thorough rinse with water. The length of time following administration at which light exposure takes place (incubation time) will generally depend on the nature of the composition and the nature of the derivative of 5-ALA or the skin compatible salt thereof. Usually, the incubation time is up to 6 hours. However, preferably it will be less than 2 hours. Still more preferably the incubation time is 0 to 90 minutes, e.g. 5 to 90 minutes, preferably 30 to 90 minutes, and more preferably 10 to 60 minutes. In one aspect of the invention, light exposure may be effected immediately after administration of the composition, i.e. the incubation time may be a matter of only minutes, e.g. up to 10 minutes, more preferably up to 5 minutes or may effectively be zero in the case where administration and light treatment occur simultaneously.

In the methods and uses of the composition, multiple treatments may be given, e.g. daily, weekly or monthly treatments. The treatment frequency will vary widely depending on, for example, the level of (photo)aging, the nature of the composition and the nature of the light treatment.

Hence in one embodiment, the composition is applied daily and the light treatment is carried out by exposure to natural light sources such as daylight or sunlight or to common artificial light sources such as home light or office light. A composition to be used in such a way may also contain sunscreens, e.g. physical and chemical UVA/UVB-filters in an amount which is common in day creams and lotions or may contain pigments which are commonly used in skin foundations and tinted moisturizers.

In another embodiment, the composition is applied 1 to 5 times, preferably 2 to 4 times in total and once a month, i.e. with a one month period between the treatments, and the light treatment is carried out by exposure to common artificial light sources such as home light or office light or by exposure to specific artificial light sources such as LED lamp systems, lasers or intense pulsed light. After having had a treatment as described before, a subject should protect his/her skin from exposure to the sun, preferably in the first 24 hours after such treatment. This may be achieved by the use of sunscreens and protective clothing such as hats (in the case of a facial treatment), gloves (in the case of a hand treatment), long trousers or sleeves (in the case of leg and arm treatments) or scarves (in the case of a neck treatment).

Hence another aspect of the invention is a method of cosmetic treatment carried out on a subject, preferably a human, said method comprising the following steps:
(i) administering to the skin of said subject a composition comprising
  a) 2% by weight or less of 5-ALA, a derivative of 5-ALA or skin compatible salts thereof b) 70% by weight or more of water;
c) 2-25% by weight of at least one lipid carrier; and
d) one or more emulsifiers (ii) optionally waiting for a time period;
(iii) optionally removing the composition from said skin; and
(iv) exposing said skin to light.

In a preferred embodiment, said cosmetic treatment is for reducing the appearance of crow's feet, dark circles, fine lines, wrinkles for decreasing pore size and for improving skin firmness and elasticity.

Preferred embodiments of steps (i) to (iv) have been described hereinbefore.

The compositions according to the invention may be used together with other cosmetic or pharmaceutical products containing known anti-aging or anti-wrinkle agents. Such other cosmetic or pharmaceutical products may be co-administered or preferably administered after the treatment with the compositions herein described. The compositions according to the invention may also be used in combination with other cosmetic and/or therapeutic methods which are known and described in the literature for use in the treatment of (photo) aged skin, such as chemical peelings, microdermabrasions or cosmetic injectables like Botox™ or fillers.

The compositions may be commercially presented in the form of a product.

Thus, viewed from a still further aspect the invention provides a product comprising
a) 2% by weight or less of 5-ALA, a derivative of 5-ALA or skin compatible salts thereof
b) 70% by weight or more of water;
c) 2- 25% by weight of at least one lipid carrier;
d) one or more emulsifiers; and
e) instructions for the use of said composition.

Viewed from a still further aspect the invention provides a container comprising a first and a second compartment wherein said first compartment comprises a derivative of 5-ALA or skin compatible salts thereof and at least one lipid carrier and said second compartment comprises water, one or more emulsifiers and optionally at least one lipid carrier, and wherein the composition obtained by mixing the contents of said first and second compartment comprises
a) 2% by weight or less of said derivative of 5-ALA or said skin compatible salts thereof
b) 70% by weight or more of said water;
c) 2-25% by weight of said at least one lipid carrier;
d) said one or more emulsifiers; and
e) instructions for the use of said container.

Such instructions for the use of the composition or container may be printed on, for instance, an outer carton (e.g. box). Alternatively, or in addition, these may be printed on the inner container, e.g. a jar, bottle, tube etc., which contains the composition of the invention or may be provided in the form of a package insert. In a preferred embodiment, said inner container is the container according to the invention.

Preferably, the instructions present in the product of the invention describe the steps of: (i) administering the composition according to the invention to the skin, i.e. to the skin at the intended site of action, and (ii) exposing said site to light. In another embodiment, the instructions present in the product of the invention describe the steps of: (i) administering the composition according to the invention to the skin, i.e. to the skin at the intended site of action, (ii) waiting for a certain time period (incubation period), (iii) optionally removing the composition from said site and (iv) exposing said site to light. In another embodiment and where the product contains the aforementioned container, the instructions present in the product of the invention describe in addition the step of mixing the content of the compartments contained in said container.

The compositions herein described are suitable for use as cosmetic products. However, in an alternative aspect, the compositions may be used in the therapeutic treatment of skin conditions or diseases, wherein the compositions' effect is desired. As an example, rosacea is a chronic condition characterized by facial erythema which typically begins on the central face across the cheeks, nose, or forehead, but can also less commonly affect the neck, chest, ears, and scalp. In some cases, additional symptoms, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may develop. Treating rosacea varies from patient to patient depending on severity and subtypes. Mild cases are often not treated at all, or are simply covered up with normal cosmetics. The two primary modalities of rosacea treatment are topical and oral antibiotic agents. Therapy for the treatment of rosacea is not curative, and is best measured in terms of reduction in the amount of erythema and inflammatory lesions, decrease in the number, duration, and intensity of flares, and concomitant symptoms of itching, burning, and tenderness. As the condition progresses, prominent enlarged facial pores can develop. The composition of the invention may be used for the treatment of such prominent enlarged facial pores due to the composition's ability to significantly decrease pore size. The composition may thus be used in the treatment of rosacea either alone or in combination with other pharmaceutics, e.g. in combination with topical or oral antibiotics.

Hence another aspect of the invention is a method of therapeutic treatment of a skin condition or disease, preferably of rosacea, carried out on a subject, preferably a human, said method comprising the following steps:
(i) administering to the skin of said subject a composition comprising
a) 2% by weight or less of 5-ALA, a derivative of 5-ALA or skin compatible salts thereof
b) 70% by weight or more of water;
c) 2-25% by weight of at least one lipid carrier; and
d) one or more emulsifiers
(ii) optionally waiting for a time period;
(iii) optionally removing the composition from said skin; and
(iv) exposing said skin to light.

Yet another aspect of the invention is the use of a composition comprising
a) 2% by weight or less of 5-ALA, a derivative of 5-ALA or skin compatible salts thereof
b) 70% by weight or more of water;
c) 2-25% by weight of at least one lipid carrier; and
d) one or more emulsifiers
in a method of therapeutic treatment of a skin condition or disease, preferably in a method of therapeutic treatment of rosacea.

Yet another aspect of the invention is a composition comprising
a) 2% by weight or less of 5-ALA, a derivative of 5-ALA or skin compatible salts thereof
b) 70% by weight or more of water;
c) 2-25% by weight of at least one lipid carrier; and
d) one or more emulsifiers
for use in the therapeutic treatment of a skin condition or disease, preferably for use in the therapeutic treatment of rosacea.

The therapeutic treatment of a skin condition or disease, preferably the therapeutic treatment of rosacea comprises the following steps:
(i) administering to the skin of said subject a composition comprising
 a) 2% by weight or less of 5-ALA, a derivative of 5-ALA or skin compatible salts thereof
 b) 70% by weight or more of water;
 c) 2-25% by weight of at least one lipid carrier; and
 d) one or more emulsifiers
(ii) optionally waiting for a time period;
(iii) optionally removing the composition from said skin; and
(iv) exposing said skin to light.

Yet another aspect of the invention is the use of a container comprising a first and a second compartment wherein said first compartment comprises a derivative of 5-ALA or skin compatible salts thereof and at least one lipid carrier and said second compartment comprises water, one or more emulsifiers and optionally at least one lipid carrier, and wherein the composition obtained by mixing the contents of said first and second compartment comprises
 a) 2% by weight or less of said derivative of 5-ALA or said skin compatible salts thereof
 b) 70% by weight or more of said water;
 c) 2-25% by weight of said at least one lipid carrier; and
 d) said one or more emulsifiers
in a method of therapeutic treatment of a skin condition or disease, preferably in a method of therapeutic treatment of rosacea.

Yet another aspect of the invention is a container comprising a first and a second compartment wherein said first compartment comprises a derivative of 5-ALA or skin compatible salts thereof and at least one lipid carrier and said second compartment comprises water, one or more emulsifiers and optionally at least one lipid carrier, and wherein the composition obtained by mixing the contents of said first and second compartment comprises
 a) 2% by weight or less of said derivative of 5-ALA or said skin compatible salts thereof
 b) 70% by weight or more of said water;
 c) 2-25% by weight of said at least one lipid carrier; and
 d) said one or more emulsifiers
for use in the therapeutic treatment of a skin condition or disease, preferably for use in the therapeutic treatment of rosacea.

Yet another aspect of the invention is the use of a product comprising a composition comprising
 a) 2% by weight or less of 5-ALA, a derivative of 5-ALA or skin compatible salts thereof
 b) 70% by weight or more of water;
 c) 2-25% by weight of at least one lipid carrier;
 d) one or more emulsifiers; and
 e) instructions for the use of said composition
in a method of therapeutic treatment of a skin condition or disease, preferably in a method of therapeutic treatment of rosacea.

Yet another aspect of the invention is a product comprising a composition comprising
 a) 2% by weight or less of 5-ALA, a derivative of 5-ALA or skin compatible salts thereof
 b) 70% by weight or more of water;
 c) 2-25% by weight of at least one lipid carrier;
 d) one or more emulsifiers; and
 e) instructions for the use of said composition
in the therapeutic treatment of a skin condition or disease, preferably the therapeutic treatment of rosacea.

Yet another aspect of the invention is the use of a product comprising a container comprising a first and a second compartment wherein said first compartment comprises a derivative of 5-ALA or skin compatible salts thereof and at least one lipid carrier and said second compartment comprises water, one or more emulsifiers and optionally at least one lipid carrier, and wherein the composition obtained by mixing the contents of said first and second compartment comprises
 a) 2% by weight or less of said derivative of 5-ALA or said skin compatible salts thereof
 b) 70% by weight or more of said water;
 c) 2-25% by weight of said at least one lipid carrier;
 d) said one or more emulsifiers; and
 e) instructions for the use of said container
in a method of therapeutic treatment of a skin condition or disease, preferably in a method of therapeutic treatment of rosacea.

Yet another aspect of the invention is a product comprising a container comprising a first and a second compartment wherein said first compartment comprises a derivative of 5-ALA or skin compatible salts thereof and at least one lipid carrier and said second compartment comprises water, one or more emulsifiers and optionally at least one lipid carrier, and wherein the composition obtained by mixing the contents of said first and second compartment comprises
 a) 2% by weight or less of said derivative of 5-ALA or said skin compatible salts thereof
 b) 70% by weight or more of said water;
 c) 2-25% by weight of said at least one lipid carrier;
 d) said one or more emulsifiers; and
 e) instructions for the use of said container
in the therapeutic treatment of a skin condition or disease, preferably in the therapeutic treatment of rosacea.

The invention will now be described in more detail by way of the following non-limiting examples:

EXAMPLE 1

Preparation of Compositions According to the Invention

The following oil-in-water emulsions were prepared as follows:

The water phase A was prepared by heating water to 80-85° C. and optionally adding the other phase A ingredients and homogenizing the mixture. The lipid phase B was prepared by combining the ingredients in a separate vessel, heating the combined ingredients to 80-85° C. and mixing until all solids melt. Phase B was added to phase A, mixed to uniformity and cooled to 35° C. under mixing. The ingredients C were added under mixing with good agitation until a uniform and homogeneous mixture was obtained. The mixture was cooled to 25° C., ingredients D were added and the mixture was mixed until uniform.

The prepared compositions 1 to 3 were filled into jars, composition 4 was filled into a dispenser.

Compositions 1(a)-1(d):
Cream containing 5-ALA n-hexyl ester hydrochloride (HAL HCl) in a concentration of 0.1% (a) 0.5% (b), 1% (c) and 2% (d) by weight

| | INCI name | function | % by weight |
|---|---|---|---|
| Phase A | water | | (a) 72.8 |
| | | | (b) 72.4 |
| | | | (c) 71.9 |
| | | | (d) 70.9 |

-continued

Compositions 1(a)-1(d):
Cream containing 5-ALA n-hexyl ester hydrochloride (HAL HCl) in a concentration of 0.1% (a) 0.5% (b), 1% (c) and 2% (d) by weight

| | INCI name | function | % by weight |
|---|---|---|---|
| Phase B | emulsifying wax NF | emulsifier | 12.0 |
| | behentrimonium methosulfate, cetearyl alcohol | emulsifier | 1.1 |
| | caprylic/capric triglyceride | lipid carrier | 8.0 |
| Ingredients C | 1,2 hexanediol, caprylyl glycol | antimicrobial | 1.0 |
| | butylene glycol | solvent | 5.0 |
| Ingredient D | HAL HCl | | (a) 0.1 |
| | | | (b) 0.5 |
| | | | (c) 1 |
| | | | (d) 2 |

Compositions 2(a)-2(c):
Cream containing 5-ALA n-hexyl ester hydrochloride (HAL HCl) in a concentration of 0.1% (a) 0.5% (b), and 1% (c) by weight

| | INCI name | function | % by weight |
|---|---|---|---|
| Phase A | water | | (a) 81.65 |
| | | | (b) 81.25 |
| | | | (c) 80.75 |
| | sclerotium gum | viscosity modifier | 0.25 |
| Phase B | cetearyl alcohol, ceteareth-20 | emulsifier | 3.50 |
| | behentrimonium methosulfate, cetyl alcohol, butylene glycol | emulsifier | 2.00 |
| | caprylic/capric triglyceride | lipid carrier | 8.00 |
| | cetyl alcohol | co-emulsifier | 3.50 |
| Ingredients C | 1,2 hexanediol, caprylyl glycol | antimicrobial | 0.50 |
| | phenoxyethanol | preservative | 0.50 |
| Ingredient D | HAL HCl | | (a) 0.1 |
| | | | (b) 0.5 |
| | | | (c) 1 | pH of compositions: 2(a): 4.68; pH of 2(b): 4.34; pH of 2(c): 4.01

Composition 3
Cream containing 5-ALA n-hexyl ester hydrochloride (HAL HCl) in a concentration of 0.5% by weight

| | INCI name | function | % by weight |
|---|---|---|---|
| Phase A | water | | 81.05 |
| | sclerotium gum | viscosity modifier | 0.25 |
| Phase B | cetearyl alcohol, ceteareth-20 | emulsifier | 3.50 |
| | behentrimonium methosulfate, cetyl alcohol, butylene glycol | emulsifier | 2.00 |
| | caprylic/capric triglyceride | lipid carrier | 8.00 |
| | cetyl alcohol | co-emulsifier | 3.50 |
| Ingredients C | 1,2 hexanediol, caprylyl glycol | antimicrobial | 0.50 |
| | phenoxyethanol | preservative | 0.50 |
| | HAL HCl | | 0.50 |
| Ingredients D | Citric acid | pH adjuster | 0.10 |
| | Sodium citrate | pH adjuster | 0.10 | pH of composition 3: 3.89

Composition 4
Lotion containing 5-ALA n-hexyl ester hydrochloride (HAL HCl) in a concentration of 0.5% by weight

| | INCI name | function | % by weight |
|---|---|---|---|
| Phase A | water | | 87.86 |
| | sclerotium gum | viscosity modifier | 0.07 |
| Phase B | cetearyl alcohol, ceteareth-20 | emulsifier | 1.00 |
| | behentrimonium methosulfate, cetyl alcohol, butylene glycol | emulsifier | 0.57 |
| | caprylic/capric triglyceride | lipid carrier | 8.00 |
| | cetyl alcohol | co-emulsifier | 1.00 |
| Ingredients C | 1,2 hexanediol, caprylyl glycol | antimicrobial | 0.50 |
| | phenoxyethanol | preservative | 0.50 |
| Ingredient D | HAL HCl | | 0.50 |

EXAMPLE 2

Preparation of Compositions According to the Invention

The following oil-in-water emulsions were prepared as follows:

Phase C:

Phase A and phase B* were prepared separately and combined to phase C.

Phase A was prepared by heating water to 80-85° C., adding the viscosity modifier and homogenizing the mixture. Phase B* was prepared by combining the ingredients in a separate vessel, heating the combined ingredients to 80-85° C. and mixing until all solids melt. Phase B* was added to phase A, mixed to uniformity and cooled to 35° C. under mixing. Ingredients C were added under mixing with good agitation until a uniform and homogeneous mixture was obtained.

Lipid Phase D:

HAL HCl was suspended in the lipid carrier.

Phase C and phase D were filled into the compartments of a two-compartment container comprising a first large compartment and a second small compartment which are separated from each other by a breakable plastic seal and further comprising a removable tip. 1.83 g of phase C was filled into large compartment and 0.177 g of phase D was filled into the small compartment of the two-compartment container. The phases were mixed inside the intact two-compartment container to produce a composition according to the invention: pressure was exerted on the large compartment which resulted in breaking the seal and forcing phase C from the large compartment into the small compartment. The two phases were mixed by squeezing the composition back and forth between the compartments. The so-produced composition was removed from the container by removing the tip. The amount of so-produced composition (2 g) was suitable for a single treatment of the face.

Composition 5
Cream containing 5-ALA n-hexyl ester hydrochloride (HAL HCl) in a concentration of 0.5% by weight

| Phase C: | | | |
|---|---|---|---|
| | INCI name | function | % by weight |
| Phase A | water | | 82.071 |
| | sclerotium gum | viscosity modifier | 0.253 |

Composition 5
Cream containing 5-ALA n-hexyl ester hydrochloride (HAL HCl)
in a concentration of 0.5% by weight

| | INCI name | function | % by weight |
|---|---|---|---|
| Phase B* | cetearyl alcohol, ceteareth-20 | emulsifier | 3.535 |
| | behentrimonium methosulfate, cetyl alcohol, butylene glycol | emulsifier | 2.020 |
| | caprylic/capric triglyceride | lipid carrier | 7.576 |
| | cetyl alcohol | co-emulsifier | 3.535 |
| Ingredient C | 1,2 hexanediol, caprylyl glycol | antimicrobial | 0.505 |
| | phenoxyethanol | preservative | 0.505 |

Phase D:

| INCI name | function | % by weight |
|---|---|---|
| caprylic/capric triglyceride | lipid carrier | 94.118 |
| HAL HCl | | 5.882 |

Mixed phases C and D, i.e. composition 5:

| INCI name | function | % by weight |
|---|---|---|
| water | | 75.09 |
| sclerotium gum | viscosity modifier | 0.23 |
| cetearyl alcohol, ceteareth-20 | emulsifier | 3.23 |
| behentrimonium methosulfate, cetyl alcohol, butylene glycol | emulsifier | 1.85 |
| caprylic/capric triglyceride | lipid carrier | 14.93 |
| cetyl alcohol | co-emulsifier | 3.23 |
| 1,2 hexanediol, caprylyl glycol | antimicrobial | 0.46 |
| phenoxyethanol | preservative | 0.46 |
| HAL HCl | | 0.50 |

Composition 6
Lotion containing 5-ALA n-hexyl ester hydrochloride (HAL HCl)
in a concentration of 0.5% by weight Phase C:

| | INCI name | function | % by weight |
|---|---|---|---|
| Phase A | water | | 96.022 |
| | sclerotium gum | viscosity modifier | 0.077 |
| Phase B* | cetearyl alcohol, ceteareth-20 | emulsifier | 1.093 |
| | behentrimonium methosulfate, cetyl alcohol, butylene glycol | emulsifier | 0.623 |
| | cetyl alcohol | co-emulsifier | 1.093 |
| Ingredients C | 1,2 hexanediol, caprylyl glycol | antimicrobial | 0.546 |
| | phenoxyethanol | preservative | 0.546 |

Phase D:

| INCI name | function | % by weight |
|---|---|---|
| caprylic/capric triglyceride | lipid carrier | 94.118 |
| HAL HCl | | 5.882 |

Mixed phases C and D, i.e. composition 6:

| INCI name | function | % by weight |
|---|---|---|
| water | | 87.86 |
| sclerotium gum | viscosity modifier | 0.07 |
| cetearyl alcohol, ceteareth-20 | emulsifier | 1.00 |
| behentrimonium methosulfate, cetyl alcohol, butylene glycol | emulsifier | 0.57 |
| caprylic/capric triglyceride | lipid carrier | 8.00 |
| cetyl alcohol | co-emulsifier | 1.00 |
| 1,2 hexanedrol, caprylyl glycol | antimicrobial | 0.50 |
| phenoxyethanol | preservative | 0.50 |
| HAL HCl | | 0.50 |

EXAMPLE 3

Stability of the Composition According to the Invention 5 g of composition 2(b), a cream which comprises 0.5% HAL HCl was prepared as described in Example 1.

5 g of a comparison composition comprising 0.5% HAL HCl was prepared by mixing HAL HCl with Unguentum M® (Almirall Ltd, UK). According to the manufacturer's information, Unguentum M® is a cream formulation comprising colloidal anhydrous silica 0.1%, liquid paraffin 3%, white soft paraffin 32%, cetostearyl alcohol 9%, polysorbate 40 6%, glycerol monostearate 3%, medium-chain triglycerides 2%, sorbic acid 0.2%, propylene glycol 5% and water q.s. for 100%, i.e. about 39.7%.

Freshly prepared, both compositions appeared white. Each composition was divided in two portions of equal weight and transferred to 20 ml screw-cap vials. One set of samples was kept at room temperature and the other at 37° C. The visual appearance of the samples was assessed on day 5 and on day 28.

| | Day 5 Appearance | Day 28 Appearance |
|---|---|---|
| 2(b) Room temperature | White | White |
| 2(b) 37° C. | White | White |
| Comparison Room temperature | Off-white | Off-white |
| Comparison 37° C. | Off-white | Off-white |

In order to assess whether the discoloration is dependent on the HAL HCl concentration, 5 g of composition 7, a cream which comprises 3% HAL HCl were prepared as described in Example 1 and 5 g of a comparison cosmetic composition comprising 3% HAL HCl were prepared by mixing HAL HCl with Unguentum. M®.

Composition 7:
Cream containing 3% HAL HCl

| | INCI name | function | % by weight |
|---|---|---|---|
| Phase A | water | | 78.75 |
| | sclerotium gum | viscosity modifier | 0.25 |
| Phase B | cetearyl alcohol, ceteareth-20 | emulsifier | 3.50 |
| | behentrimonium methosulfate, cetyl alcohol, butylene glycol | emulsifier | 2.00 |
| | caprylic/capric triglyceride | lipid carrier | 8.00 |
| | cetyl alcohol | co-emulsifier | 3.50 |
| Ingredients C | 1,2 hexanediol, caprylyl glycol | antimicrobial | 0.50 |
| | phenoxyethanol | preservative | 0.50 |

Composition 7:
Cream containing 3% HAL HCl

| INCI name | function | % by weight |
|---|---|---|
| Ingredient D | HAL HCl | 3.00 |

Freshly prepared, both compositions appeared white. Each composition was divided in two portions of equal weight and transferred to 20 ml screw-cap vials. One set of samples was kept at room temperature and the other at 37° C. The visual appearance of the samples was assessed on day 5 and on day 28.

| | Day 5 Appearance | Day 28 Appearance |
|---|---|---|
| Composition 7 Room temperature | White | White |
| Composition 7 37° C. | White | White |
| Comparison Room temperature | Off-white | Off-white |
| Comparison 37° C. | Off-white | Yellow, a small amount of yellow oil had formed on top of the composition |

From the data above, it can be expected that compositions according to the invention comprising HAL HCl in concentrations of 2% by weight and less will be stable, i.e. keep their visual appearance and color at least for 4 weeks at room temperature. This is a very important aspect of a cosmetic product since, unlike for pharmaceuticals for which cold storage is acceptable to vendors and consumers, cosmetic products need to be stable at room temperature, i.e. have an adequate shelf life, without showing signs of disintegration and/or discoloration.

EXAMPLE 4

Stability of the Composition According to the Invention

Oil-in-water emulsions compositions 8(a)-(c) to 12(a)-(c) were prepared as described in Example 1.

Compositions 8(a)-8(c):
8(a): containing 5-ALA methyl ester mesylate (MAL MES) in a concentration of 0.5% by weight; 8(b): containing 5-ALA n-hexyl ester napsylate (HAL NAPS) in a concentration of 0.5% by weight; 8(c): containing 5-ALA n-hexyl ester hydrochloride (HAL HCl) in a concentration of 0.5% by weight

| | INCI name | function | % by weight |
|---|---|---|---|
| Phase A | water | | 81.25 |
| | sclerotium gum | viscosity modifier | 0.25 |
| Phase B | cetearyl alcohol, ceteareth-20 | emulsifier | 3.50 |
| | behentrimonium methosulfate, cetyl alcohol, butylene glycol | emulsifier | 2.00 |
| | caprylic/capric triglyceride | lipid carrier | 8.00 |
| | cetyl alcohol | co-emulsifier | 3.50 |
| Ingredients C | 1,2 hexanediol, caprylyl glycol | antimicrobial | 0.50 |
| | phenoxyethanol | preservative | 0.50 |
| Ingredient D | MAL MES or HAL NAPS or HAL HCl | | 0.5 |

Compositions 9(a)-9(c):
9(a): containing 5-ALA methyl ester mesylate (MAL MES) in a concentration of 0.5% by weight; 9(b): containing 5-ALA n-hexyl ester napsylate (HAL NAPS) in a concentration of 0.5% by weight; 9(c): containing 5-ALA n-hexyl ester hydrochloride (HAL HCl) in a concentration of 0.5% by weight

| | INCI name | function | % by weight |
|---|---|---|---|
| Phase A | water | | 84.75 |
| | sclerotium gum | viscosity modifier | 0.25 |
| Phase B | cetearyl alcohol, ceteareth-20 | emulsifier | 3.50 |
| | behentrimonium methosulfate, cetyl alcohol, butylene glycol | emulsifier | 2.00 |
| | safflower oil | lipid carrier | 5.00 |
| | cetyl alcohol | co-emulsifier | 3.50 |
| Ingredients C | 1,2 hexanediol, caprylyl glycol | antimicrobial | 0.50 |
| | phenoxyethanol | preservative | 0.50 |
| Ingredient D | MAL MES or HAL NAPS or HAL HCl | | 0.5 |

Compositions 10(a)-10(c):
10(a): containing 5-ALA methyl ester mesylate (MAL MES) in a concentration of 0.5% by weight; 10(b): containing 5-ALA n-hexyl ester napsylate (HAL NAPS) in a concentration of 0.5% by weight; 10(c): containing 5-ALA n-hexyl ester hydrochloride (HAL HCl) in a concentration of 0.5% by weight

| | INCI name | function | % by weight |
|---|---|---|---|
| Phase A | water | | 74.75 |
| | sclerotium gum | viscosity modifier | 0.25 |
| Phase B | cetearyl alcohol, ceteareth-20 | emulsifier | 3.50 |
| | behentrimonium methosulfate, cetyl alcohol, butylene glycol | emulsifier | 2.00 |
| | mineral oil | lipid carrier | 15.00 |
| | cetyl alcohol | co-emulsifier | 3.50 |
| Ingredients C | 1,2 hexanediol, caprylyl glycol | antimicrobial | 0.50 |
| | phenoxyethanol | preservative | 0.50 |
| Ingredient D | MAL MES or HAL NAPS or HAL HCl | | 0.5 |

Compositions 11(a)-11(c):
11(a): containing 5-ALA methyl ester mesylate (MAL MES) in a concentration of 0.5% by weight; 11(b): containing 5-ALA n-hexyl ester napsylate (HAL NAPS) in a concentration of 0.5% by weight; 11(c): containing 5-ALA n-hexyl ester hydrochloride (HAL HCl) in a concentration of 0.5% by weight

|  | INCI name | function | % by weight |
|---|---|---|---|
| Phase A | water |  | 87.25 |
|  | sclerotium gum | viscosity modifier | 0.25 |
| Phase B | cetearyl alcohol, ceteareth-20 | emulsifier | 3.50 |
|  | behentrimonium methosulfate, cetyl alcohol, butylene glycol | emulsifier | 2.00 |
|  | stearic acid | lipid carrier | 2.50 |
|  | cetyl alcohol | co-emulsifier | 3.50 |
| Ingredients C | 1,2 hexanediol, caprylyl glycol | antimicrobial | 0.50 |
|  | phenoxyethanol | preservative | 0.50 |
| Ingredient D | MAL MES or HAL NAPS or HAL HCl |  | 0.5 |

Compositions 12(a)-12(c):
12(a): containing 5-ALA methyl ester mesylate (MAL MES) in a concentration of 0.5% by weight; 12(b): containing 5-ALA n-hexyl ester napsylate (HAL NAPS) in a concentration of 0.5% by weight; 12(c): containing 5-ALA n-hexyl ester hydrochloride (HAL HCl) in a concentration of 0.5% by weight

|  | INCI name | function | % by weight |
|---|---|---|---|
| Phase A | water |  | 81.25 |
|  | sclerotium gum | viscosity modifier | 0.25 |
| Phase B | cetearyl alcohol, ceteareth-20 | emulsifier | 3.50 |
|  | behentrimonium methosulfate, cetyl alcohol, butylene glycol | emulsifier | 2.00 |
|  | jojoba oil | lipid carrier | 8.00 |
|  | cetyl alcohol | co-emulsifier | 3.50 |
| Ingredients C | 1,2 hexanediol, caprylyl glycol | antimicrobial | 0.50 |
|  | phenoxyethanol | preservative | 0.50 |
| Ingredient D | MAL MES or HAL NAPS or HAL HCl |  | 0.5 |

5 g of each of the compositions 8(a)-(c) to 12(a)-(c) were prepared.

5 g of comparison compositions comprising 0.5% MAL MES, 0.5% HAL NAPS or 0.5% HAL HCl were prepared by mixing MAL MES, HAL NAPS or HAL HCl with Unguentum M® (Almirall Ltd, UK).

Freshly prepared, all compositions appeared white. Each composition was divided in two portions of equal weight and transferred to 20 ml screw-cap vials. One set of samples was kept at room temperature and the other at 37° C. The visual appearance of the samples was assessed on day 5 and on day 28.
Results:

Compositions (a) containing 5-ALA methyl ester mesylate (MAL MES) in a concentration of 0.5% by weight:

| Composition | Temperature | Day 5 Appearance | Day 28 Appearance |
|---|---|---|---|
| 8(a) | Room temperature | White | White |
|  | 37° C. | White | White |
| 9(a) | Room temperature | White | White |
|  | 37° C. | White | White |
| 10(a) | Room temperature | White | White |
|  | 37° C. | White | White |
| 11(a) | Room temperature | White | White |
|  | 37° C. | White | White |
| 12(a) | Room temperature | White | White |
|  | 37° C. | White | White |
| Unguentum M® | Room temperature | Slightly discolored | Pale tan |
|  | 37° C. | Slightly discolored | Pale tan |

Compositions (b) containing 5-ALA n-hexyl ester napsylate (HAL NAPS) in a concentration of 0.5% by weight

| Composition | Temperature | Day 5 Appearance | Day 28 Appearance |
|---|---|---|---|
| 8(b) | Room temperature | White | White |
|  | 37° C. | White | White |
| 9(b) | Room temperature | White | White |
|  | 37° C. | White | White |
| 10(b) | Room temperature | White | White |
|  | 37° C. | White | White |
| 11(b) | Room temperature | White | White |
|  | 37° C. | White | White |
| 12(b) | Room temperature | White | White |
|  | 37° C. | White | White |
| Unguentum M® | Room temperature | Slightly discolored | Pale tan |
|  | 37° C. | Slightly discolored | Pale tan |

Compositions (c) containing 5-ALA n-hexyl ester hydrochloride (HAL HCl) in a concentration of 0.5% by weight

| Composition | Temperature | Day 5 Appearance | Day 28 Appearance |
|---|---|---|---|
| 8(c) | Room temperature | White | White |
|  | 37° C. | White | White |
| 9(c) | Room temperature | White | White |
|  | 37° C. | White | White |
| 10(c) | Room temperature | White | White |
|  | 37° C. | White | White |
| 11(c) | Room temperature | White | White |
|  | 37° C. | White | White |
| 12(c) | Room temperature | White | White |
|  | 37° C. | White | White |
| Unguentum M® | Room temperature | Slightly discolored | Pale tan |
|  | 37° C. | Slightly discolored | Pale tan |

EXAMPLE 5

Cosmetic Efficacy I

Composition 2(b) which had been prepared as described in Example 1 was tested in a pilot study on the skin of volunteer subjects to determine its safety and cosmetic efficacy.

Sixteen female subjects, ranging in age from 40 to 60 years, were enrolled. All of them possessed skin color that could be classified as Fitzpatrick I to III, as determined by Chromameter readings. Further, all of them exhibited visible signs of aging and possessed a minimum amount of moderate facial photodamage, as determined by a trained technician utilizing VISTA CR™ digital UV photographs.

Protocol:

To standardize the skin condition of the study population at baseline and minimize variability attributable to use of different skin care regimens, subjects participated in a 7-day (±3 days) conditioning period. Each subject was provided with written study instructions, a sunscreen, and a bar of Purpose® soap (Johnson & Johnson Consumer Companies, Inc.) to use at least once daily on the entire face and for all facial cleansing during the conditioning phase of the study and for the duration of the study.

Following the conditioning period, subjects returned to the study facility for baseline evaluations with a clean and make-up free face. A pre-treatment questionnaire related to self-evaluation of the skin and its condition was completed by each subject. Subjects were allowed to acclimate to ambient laboratory conditions for a period of 30 minutes prior to baseline evaluations. Following the acclimation period, certain skin parameters were determined by objective measurements according to usual cosmetic industry standards:

Skin color was determined on two separate areas of the face with a Chromameter (Konica Minolta), wherein color is expressed numerically in the L*a*b* color space; In this color space, L* is the luminance and gives the relative brightness from total black (L*=0) to total white (L*=100). Theoretically, a skin lightening effect will increase L*. The a* value represents the balance between the reds and the greens. The other chromatic coordinate, b*, represents the balance between the yellows and the blues. Changes in the color variables measured by the Chromameter reflect changes in the appearance of skin color features such as dark circles under the eyes, blotchiness, facial discoloration, age spots, radiance, or brightness of the skin or other skin pigmentation. Measurements are obtained by placing the hand held measuring head perpendicular to the skin. Three consecutive readings will be obtained within each test site and averaged. Chromameter measurements were taken on two separate areas of the face. One test site of an area exhibiting even skin tone and one test site of an area exhibiting uneven skin one. The areas were marked by measuring from anatomical landmarks. Test site identification was recorded on a test site locator document. The area exhibiting even skin tone was utilized for the evaluation of skin radiance/luminosity and evenness of skin tone in conjunction with the area exhibiting uneven skin tone.

Skin surface topography was determined in the designated crow's feet area with the PRIMOS 3D optical scanning system (GF Messtechnick GmbH). The variation in surface topography is expressed in terms of roughness parameters, Ra, Rz, and Rmax. Ra is the average roughness and provides a measure of the mean height of surface variations relative to the average height of the surface of the skin in the evaluated skin area. These features can be measured to an accuracy of 1 micrometer. Rz is equivalent to the average of the greatest differences from peak to valley across the profile. Rmax is the maximum difference between the highest measured peak and the lowest valley in the skin profile. Each of these variables increases with increasing skin roughness and, inversely, decreases with improved smoothness of the skin surface.

Pore size of five visible pores was determined in an area exhibiting large pores by the use of a Hi-Scope® video microscope (KH-2200, Hirox Company Ltd., Japan). The area was marked by measuring from anatomical landmarks. Test site identification was recorded on a test site locator document. Hi-Scope® images of the same location were obtained at designated study intervals. At the conclusion of each designated study interval, the images were reviewed and the size of each of the five pores was measured. The five measurements were averaged for a total pore size score for each designated study interval.

Skin elasticity/firmness was determined by Cutometer® measurements (Courage+Khazaka electronic GmbH) on the upper cheekbone directly below the outer corner of the eye. The instrument measures the vertical deformation of the surface of the skin as it is pulled by a vacuum suction (500 mm Hg) through a small probe aperture. The suction is generated by a variable vacuum pump, and the depth of penetration of the skin into the probe is measured optically with an accuracy of 0.01 mm. The probe is attached to a computer, which controls the vacuum application and determines skin deformation at defined intervals: The final distention, Uf, measured at 10 seconds, the immediate distention, Ue, measured at 0.1 seconds, the delayed distention, Uv and the immediate retraction, Ur. The deformation parameters are extrinsic parameters dependent on skin thickness. In order to circumvent the measurement of skin thickness, the following ratios are used to evaluate the elastic nature of the skin: Ur/Uf is biological elasticity of the skin. It measures the ability of the skin to regain its initial configuration after deformation. A value of one would indicate 100% elasticity. Ur/Ue is a measure of the net elasticity of the skin. Uv/Ue is the ratio between delayed and immediate deformation, i.e. it is the viscoelastic to elastic ratio. An increase in the value of this ratio indicates that there has been an increase in the viscoelastic portion of the deformation and/or relative decrease of the elastic part. Measurements are obtained by holding the probe firmly against the surface of the skin. The vacuum pump suctions the skin into a small opening and the probe measures the height to which the skin is distended. Measurements are automatically produced in triplicate, by running through three twenty-second cycles. Each cycle is made up of a suction phase, where the skin is sucked into the probe, and a relaxation phase, where the suction stops and the skin is released. Data is electronically imported into the computer, where ratio values are calculated. Readings are displayed and then manually transcribed onto a score sheet. Cutometer® measurements were taken on the upper cheek bone directly below the outer corner of the eye on the designated side of the face.

Digital clinical photographs were taken using a Canfield's VISIA-CR™ photo imaging equipment. Features of the equipment include an adjustable forehead rest, a stationary chin cup with multiple settings, three positioning mirrors, and image preview tools to assure proper repositioning of the subject from baseline to treatment evaluation intervals without obscuring the area of interest. Video preview and display overlay tools further facilitate consistent positioning of each subject. This ensures that any observed changes are attributable to the applied treatment. Three full-face (cross-polarized, standard & UV fluorescence) images, and two side-view images (standard & cross-polarized) were captured at designated study intervals. Digital photographs captured with standard and cross-polarized lighting were utilized for documentation purposes only, and UV fluorescence images were utilized for grading of photodamage.

After baseline evaluations, the cosmetic treatment with composition 2(b) was carried out as follows:
1. The face was washed with Purpose® soap followed by thorough rinse with water. The face was gently dried with a clean towel or single use paper towel.
2. About 2 grams of composition 2(b) was applied to all areas of the face except the areas that will be covered with goggles during illumination.

3. The composition was left on the face for 1 hour (incubation time)
4. The face was washed with Purpose® soap followed by thorough rinse with water. The face was gently dried with a clean towel or single use paper towel.
5. Immediately thereafter, the face was exposed to red light of 635 nm (Aktilite® 128, Galderma) for 8 minutes and 36 seconds. The subjects wore goggles during illumination and the light source was positioned 4 inches from the face.
6. After illumination, the face was washed with cold water and sunscreen was applied
7. Subjects were instructed to wear a sun hat when leaving the study facilities and to avoid outdoor light for 48 hours post treatment. If outdoor activities were necessary, subjects were instructed to wear sunscreen, a hat and sunglasses.

The above-described cosmetic treatment was carried out three times with a month interval between each treatment. Subjects were followed up 48 hours after each treatment for irritation evaluations. Before the second and third treatment and one month after the third treatment, the same skin parameters as for the baseline evaluation were determined. From the 16 subjects, 10 subjects completed the study.

Results:
Objective Tolerance Evaluation:

Mainly only mild irritation of the skin in the form of mild facial erythema, mild facial edema and mild dryness was observed. Only one subject did exhibit moderate erythema at the 48 hour post-1 month evaluation (after $2^{nd}$ treatment) and the 48 hour post-2 month evaluation (after $3^{rd}$ treatment), and one subject exhibited severe erythema at the 48 hour post-1 month evaluation (after $2^{nd}$ treatment). Only one subject did exhibit moderate edema at the 48 hour post-2 month evaluation (after $3^{rd}$ treatment).

Skin Color:

No statistically significant differences in Chromameter L* values were observed for either even skin tone or uneven skin tone at any of the post-treatment evaluations. Statistically significant increases in Chromameter a* values were observed for even skin tone at the 3 month evaluation compared to baseline, which suggests a change in hue in the direction of green to red. No statistically significant differences in Chromameter a* values were observed for uneven skin tone at any of the post-treatment evaluations. Statistically significant increases in Chromameter b* values were observed for even skin tone at the 2 month evaluation, and for uneven skin tone at each post-treatment evaluation compared to baseline, which suggests a change in hue in the direction of blue to yellow. Statistically significant improvement for evening skin tone after the first treatment was observed, i.e. bringing uneven skin closer to even skin Skin Surface Topography:

Decreases in each PRIMOS 3D (Ra, Rz and Rmax) parameter observed at each post-treatment evaluation revealed a trend towards an improvement in skin smoothness.

Pore Size Assessments:

Immediately following a single treatment, a statistically significant decease in Hi-Scope® pore size measurements was observed compared to baseline.

Skin Elasticity/Firmness:

Statistically significant decreases in the Cutometer® parameter Uf (final distention/skin extensibility) measurements were observed at the 2 and 3 month evaluations compared to baseline, which is indicative of an improvement in skin elasticity.

Visual Assessment of Photodamaged Facial Skin Utilizing Digital Images:

A statistically significant decrease Visual Analog Scale (VAS) scores was observed at the 3 month evaluation compared to baseline, which is indicative of an improvement in photodamaged facial skin.

Questionnaires:

Questionnaires completed by subjects before the first cosmetic treatment and 1 month, 2 months and 3 month, i.e. after the first, second and third treatment revealed that a statistically significant portion of the test population reported smoother skin at the 2 month evaluation (following 2 treatments), and softer skin at the 3 month evaluation (following 3 treatments).

Summary

Under the conditions of this pilot study and in this limited study population, application of composition 2(b) in conjunction with illumination demonstrated statistically significant improvement of facial skin pore size, skin elasticity and photodamage. A trend towards an improvement in skin smoothness was further observed. The subjects felt that their skin had become smoother and softer. Furthermore, application the cosmetic treatment using composition 2(b) in conjunction with red-light illumination was reasonably well tolerated.

EXAMPLE 6

Cosmetic Efficacy II

Composition 5 which had been prepared as described in Example 2 and which was provided in a two-compartment container and mixed before administration to the skin was tested in a consumer study on the skin of volunteer subjects to determine its safety and its cosmetic efficacy compared to skin illumination only.

One hundred and twenty female subjects, ranging in age from 36 to 60 years, were enrolled. All of them possessed skin color that could be classified as Fitzpatrick I to III, as determined by Chromameter readings. Further, all of them exhibited visible signs of aging and possessed a minimum amount of moderate facial photodamage, as determined by a trained technician utilizing VISIA CR™ digital UV photographs.

Protocol:

The subjects were randomized into two cells: subjects assigned to Cell 1 received skin illumination only and subjects assigned to Cell 2 received skin illumination after administration and incubation of composition 5. The treatment protocol of Cell 2 was identical to Example 5 while in the treatment protocol of Cell 1, steps 2-4 were skipped. The cosmetic treatment was carried out three times with a month interval between each treatment. Subjects were followed up 48 hours and 1 week after each treatment for irritation evaluations. Further at 1 month, 2 months, 3 months, 4 months and 5 months after baseline, same skin parameters as for the baseline evaluation were determined. From the 120 subjects, a total of 101 subjects completed the study, 19 subjects were discontinued from study participation due to a missed study visit. No subjects were discontinued due to an intolerance of composition 2(b).

Results:
Objective Tolerance Evaluation:

Mild facial erythema was observed in a limited portion of the subjects in Cell 1 and Cell 2 throughout the study. Moderate short-term persisting facial erythema was observed in a very limited portion (less than 10%) of the subjects in Cell 2, two days following the first (3 subjects), second (2 subjects) and third treatment (4 subjects) and seven days following the second treatment (1 subject). Mild short-term persisting facial edema was observed in a very limited portion (about 10%) of the subjects in Cell 2 two days following the first (4 subjects), second (3 subjects) and third treatment (5 subjects). Mild facial dryness was observed in a limited portion of the subjects in Cell 1 and Cell 2 throughout the study. Moderate facial dryness was observed in one subject in Cell 1 seven days following the third treatment, and in a very limited portion (less than 10%) of the subjects in Cell 2, two and seven days following the first and second treatment, as well as in one subject two days following the third treatment Skin Color:

No statistically significant differences in Chromameter (L*, a*, b*) measurements between cells for either test area (even skin tone and uneven skin tone) were observed at baseline. Statistically significant differences in Chromameter L* and a* measurements between test areas (even skin tone and uneven skin tone) within each cell was observed at baseline. Cell 1: Decreases in Chromameter L* measurements at the two month evaluation were significantly greater for the even skin tone then the uneven skin tone, when comparing to baseline. The differences in change from baseline for Chromameter a* measurements between even skin tone (increases) and uneven skin tone (decreases) were statistically significant at the two and three month evaluations. Cell 2: Increases in Chromameter a* measurements at the two month evaluation were significantly greater for the even skin tone then the uneven skin tone, when comparing to baseline. The difference in Chromameter E (total color) values between test areas (even skin tone and uneven skin tone) within Cell 2 significantly decreased (improved) at the four and five month evaluation, i.e. difference in appearance between even and uneven skin tone are leveled out.

Skin Surface Topography:

No statistically significant differences in PRIMOS 3D (Ra, Rz and Rmax) measurements between Cell 1 and Cell 2 were observed at baseline. The difference in change from baseline for the PRIMOS 3D parameter Ra between Cell 1 (decrease in Ra) and Cell 2 were statistically significant.

Pore Size Assessments:

No statistically significant differences in Hi-Scope® pore size measurements between Cell 1 and Cell 2 were observed at baseline. Decreases in Hi-Scope® pore size measurements were significantly greater for Cell 2 then Cell 1 at each post-treatment evaluation when compared to baseline (i.e. up to 5 month after the first treatment), with the exception of the two days following the 1$^{st}$ treatment evaluation.

Skin Elasticity/Firmness:

No statistically significant differences in Cutometer® (Uf and Ur/Uf) between Cell 1 and Cell 2 were observed at baseline. Cell 1: Statistically significant increases in the Cutometer® parameter Uf (final distention/skin extensibility) were observed at the four and five month post-treatment evaluations when comparing to baseline, which is indicative of a decrease in skin firmness. A statistically significant decrease in the Cutometer® ratio Ur/Uf (biological elasticity) was observed at the five month post-treatment evaluations when comparing to baseline, which is indicative of a decrease in skin elasticity. Cell 2: statistically significant decreases in the Cutometer® parameter Uf (final distention/skin extensibility) were observed at the two, three, four and five month post-treatment evaluations when comparing to baseline, which is indicative of an increase in skin firmness. A statistically significant increase in the Cutometer® ratio Ur/Uf (biological elasticity) was observed at the three month post-treatment evaluations when comparing to baseline, which is indicative of an increase in skin elasticity.

The differences in change from baseline for the Cutometer® parameter Uf (final distention/skin extensibility) between Cell 1 (increases in Uf) and Cell 2 (significant decreases in Uf) were statistically significant at the two, three, four and five month evaluation. Increases in the Cutometer® ratio Ur/Uf (biological elasticity) were significantly greater for Cell 2 then Cell 1 at the three month evaluation, when compared to baseline. In addition, the differences in change from baseline for the Cutometer® ratio Ur/Uf (biological elasticity) between Cell 1 (decreases in Ur/Uf) and Cell 2 (increases in Ur/Uf) were statistically significant at the four and five month evaluation.

Visual Assessment of Photodamaged Facial Skin Utilizing Digital Images:

A statistically significant decrease in Visual Analog Scale (VAS) scores of photodamaged facial skin for Cells 1 and 2 was observed at each post-treatment evaluation when comparing to baseline, which is indicative of an improvement in photodamaged facial skin.

Questionnaires:

| 2 independent sample t-test or Mann-Whitney test | Question | Mean difference between the two treatment cells (Cell1-Cell2)* | p-value |
|---|---|---|---|
| Comparison of differences in consumer perception between the two treatment cells at 5 month | 1. My skin feels more hydrated. | 0.71 | (p = 0.0001) |
| | 2. My skin feels more moisturized. | 0.65 | (p = 0.0006) |
| | 3. I see a reduction in wrinkles. | 0.65 | (p = 0.0093) |
| | 4. I see a reduction in fine lines. | 0.49 | (p = 0.0181) |
| | 5. I see a reduction of eye wrinkles like crow's-feet, lines, or dark circles. | 0.43 | (p = 0.0456) |
| | 6. The area around my eyes looks less puffy and fatigued. | 0.45 | (p = 0.0467) |
| | 7. My skin feels smoother. | 0.50 | (p = 0.0176) |
| | 8. My skin feels firmer. | 0.51 | (p = 0.0209) |
| | 9. My skin feels softer. | 0.57 | (p = 0.0070) |
| | 10. My skin appears to glow and look more radiant. | 0.74 | (p = 0.0008) |
| | 11. My skin looks brighter and clearer. | 0.59 | (p = 0.0062) |
| | 12. My skin looks more even toned. | 0.33 | (p = 0.1032) |
| | 13. My skin has fewer discolorations. | 0.09 | (p = 0.7626) |
| | 14. My pores look less visible. | 0.32 | (p = 0.1032) |
| | 15. My skin texture is improved. | 0.61 | (p = 0.0024) |
| | 16. I look younger. | 0.56 | (p = 0.0121) |
| | 17. I feel my skin looks more beautiful. | 0.67 | (p = 0.0024) |
| | 18. My skin feels revitalized. | 0.71 | (p = 0.0003) |
| | 19. My skin looks and feels healthier. | 0.60 | (p = 0.0032) |
| | 20. The product feels good on my skin. | 0.40 | (p = 0.0248) |
| | 21. This product is superior to what I have been using. | 0.51 | (p = 0.0140) |
| | 22. I would recommend this product to a friend. | 0.54 | (p = 0.0111) |

Shading/bold indicates statistical significance.

*Positive value indicates that Cell 2 (skin illumination and composition 5) performed significantly better than Cell 1 (skin illumination only).

Summary:

Under the conditions of this study skin illumination with application of composition 5 (Cell 2) proved to be superior over skin illumination only (Cell 1) in terms of significantly improving pore size and skin firmness and elasticity during the five month study period. Furthermore, the treatment was reasonably well tolerated. By comparing questionnaire responses completed by subjects of Cell 1 and Cell 2, a statistically significant difference in various improvements of facial skin attributes including, hydration, moisturization, fine lines, wrinkles, dark circles, puffiness, smoothness, firmness, softness, radiance, brightness, texture, revitalization and a younger, healthier appearance one month following the first treatment and throughout the five month study period was seen for Cell 2.

The invention claimed is:

1. A composition comprising
   a) 2% by weight or less of a derivative of 5-ALA or skin compatible salts thereof
   b) 70% by weight or more of water;
   c) 2-25% by weight of at least one lipid carrier; and
   d) more than one emulsifier, comprising at least one nonionic emulsifier and at least one cationic emulsifier;
      wherein said derivative of 5-ALA is a compound of formula (I)

$$R^2{}_2N-CH_2COCH_2-CH_2CO-OR^1 \quad (I)$$

wherein
   $R^1$ represents a substituted or unsubstituted alkyl group; and
   $R^2$ each independently represents a hydrogen atom or a group $R^1$.

2. The composition of claim 1 comprising a skin compatible salt of a compound of formula (I).

3. The composition of claim 1 wherein $R^1$ is $C_1$-$C_{10}$-alkyl and both $R^2$ represent hydrogen.

4. The composition of claim 3 wherein $R^1$ is $C_1$-$C_8$-alkyl.

5. The composition of claim 4 wherein $R^1$ is $C_1$-$C_6$-alkyl.

6. The composition of claim 1 wherein said at least one lipid carrier is a fat, wax, oil, free fatty acid or an ester of a fatty acid or a fatty alcohol.

7. The composition of claim 6 wherein said at least one lipid carrier is a fat.

8. The composition of claim 7 wherein the fat is a triglyceride having three identical or different, saturated or unsaturated, branched or unbranched fatty acid side chains, each having a chain length of from 6 to 24 carbon atoms.

9. The composition of claim 8 wherein the fatty acid side chains each have a length of from 8 to 18 carbon atoms.

10. The composition of claim 1 wherein said composition is an oil-in-water emulsion and the emulsifiers are oil-in-water emulsifiers.

11. The composition of claim 10 wherein the average size of the emulsified particles is >200 nm.

12. The composition of claim 11 wherein the average size of the emulsified particles is >500 nm.

13. A container comprising a first and a second compartment wherein said first compartment comprises a derivative of 5-ALA or a skin compatible salt thereof and at least one lipid carrier and said second compartment comprises water, one or more emulsifiers and optionally at least one lipid carrier, wherein a composition according to claim 1 is obtained by mixing the contents of said first and second compartments.

14. The container of claim 13, wherein at least one of the compartments comprises a visual indicator to determine proper mixing of the contents of said first and second compartment, wherein the visual indicator is a colorant or dyestuff.

15. A product comprising the composition of claim 1 together with instructions for the use of said composition.

16. A method of cosmetic treatment carried out on a subject, said method comprising the following steps:
   (i) administering to the skin of said subject the composition of claim 1; and
   (ii) exposing said skin to light.

17. The method of claim 16, further comprising at least one of the following steps between steps (i) and (ii):
   (a) waiting for a time period; and
   (b) removing the composition from said skin.

18. The method of claim 16, wherein the subject is a human.

19. The method of claim 16, wherein the composition is prepared from the container of claim 13 by combining the contents of the first and second compartments.

20. The method of claim 16, wherein the composition is prepared from the product of claim 18 in accordance with the accompanying instructions.

21. A method of treating a skin condition or skin disease in a subject, said method comprising the following steps:
   (i) administering to the skin of said subject the composition of claim 1; and
   (ii) exposing said skin to light.

22. The method of claim 21, further comprising at least one of the following steps between steps (i) and (ii):
   (a) waiting for a time period; and
   (b) removing the composition from said skin.

23. The method of claim 21, wherein the subject is a human.

24. The method of claim 21, wherein the skin condition or skin disease is rosacea.

25. The method of claim 21, wherein the composition is prepared from the container of claim 16 by combining the contents of the first and second compartments.

26. The method of claim 21, wherein the composition is prepared from the product of claim 18 in accordance with the accompanying instructions.

27. The composition of claim 1, wherein the derivative of 5-ALA or skin compatible salts thereof is 5-ALA n-hexyl ester napsylate (HAL NAPS).

28. The composition of claim 1, wherein the derivative of 5-ALA or skin compatible salts thereof is 5-ALA n-hexyl ester and skin compatible salts thereof.

29. The composition of claim 1, wherein the derivative of 5-ALA or skin compatible salts thereof is the HCl salt of 5-ALA n-hexyl ester.

30. The container of claim 13 together with instructions for the use of said container.

* * * * *